US012763227B2

(12) United States Patent
Wilson et al.

(10) Patent No.: US 12,763,227 B2
(45) Date of Patent: Oct. 13, 2026

(54) DEVICES TO REDUCE RADIATION EXPOSURE

(71) Applicant: Egg Medical, Inc., Arden Hills, MN (US)

(72) Inventors: Robert F. Wilson, Roseville, MN (US); John P. Gainor, Mendota Heights, MN (US); Blair Allen, Mendota Heights, MN (US); William J. Burmaster, Plymouth, MN (US)

(73) Assignee: Egg Medical, Inc., Arden Hills, MN (US)

( * ) Notice: Subject to any disclaimer, the term of this patent is extended or adjusted under 35 U.S.C. 154(b) by 514 days.

(21) Appl. No.: 17/969,512

(22) Filed: Oct. 19, 2022

(65) Prior Publication Data

US 2023/0126167 A1 Apr. 27, 2023

Related U.S. Application Data

(60) Provisional application No. 63/341,894, filed on May 13, 2022, provisional application No. 63/270,309, filed on Oct. 21, 2021.

(51) Int. Cl.

| | |
|---|---|
| ***G21F 3/00*** | (2006.01) |
| ***A61B 6/10*** | (2006.01) |
| ***G01D 5/14*** | (2006.01) |
| ***G01T 1/16*** | (2006.01) |

(52) U.S. Cl.

CPC ................ *G21F 3/00* (2013.01); *A61B 6/107* (2013.01); *G01D 5/142* (2013.01); *G01T 1/16* (2013.01)

(58) Field of Classification Search

None

See application file for complete search history.

(56) References Cited

U.S. PATENT DOCUMENTS

| | | | |
|---|---|---|---|
| 1,907,523 | A | 5/1933 | Egressi et al. |
| 3,308,297 | A | 3/1967 | Mansker |
| 3,984,696 | A | 10/1976 | Collica et al. |
| 4,254,341 | A | 3/1981 | Herr et al. |

(Continued)

FOREIGN PATENT DOCUMENTS

| | | | | |
|---|---|---|---|---|
| CA | 3037229 A1 * | 9/2019 | ............... | G21F 3/02 |
| CA | 3006471 A1 | 11/2019 | | |

(Continued)

OTHER PUBLICATIONS

English machine translation for CN-106618627-A (Year: 2017).*

(Continued)

*Primary Examiner* — David E Smith
*Assistant Examiner* — Alina Kaliszewski
(74) *Attorney, Agent, or Firm* — Fredrikson & Byron, P.A.

(57) ABSTRACT

A flexible radiation shielding system for reducing scatter radiation that may arise during the performance of certain medical imaging procedures. A multi-articulated shielding system comprising two or more shielding elements hingedly coupled to each other to thereby enable a user to bend the shielding system into a desired shape to provide radiation shielding protection to workers. A flexible radiation shielding system may comprise a plurality of shielding elements that are, for example, translucent, transparent, clear, etc., to enable workers to view objects through the shielding elements.

15 Claims, 16 Drawing Sheets

(56) References Cited

U.S. PATENT DOCUMENTS

| | | | | |
|---|---|---|---|---|
| 4,280,056 | A | 7/1981 | Renshaw | |
| 4,581,538 | A | 4/1986 | Lenhart | |
| D300,945 | S | 5/1989 | Fleming et al. | |
| 4,923,162 | A | 5/1990 | Fleming et al. | |
| 4,965,456 | A | 10/1990 | Huettenrauch et al. | |
| 5,006,718 | A | 4/1991 | Lenhart | |
| 5,015,864 | A | 5/1991 | Maleki | |
| 5,090,044 | A | 2/1992 | Kobayashi | |
| 5,417,225 | A | 5/1995 | Rubenstein et al. | |
| 5,981,964 | A | 11/1999 | Mcauley et al. | |
| 6,325,538 | B1 * | 12/2001 | Heesch | G21F 3/00 250/517.1 |
| 6,448,571 | B1 | 9/2002 | Goldstein | |
| 6,471,167 | B1 | 10/2002 | Myers et al. | |
| 6,653,648 | B2 | 11/2003 | Goldstein | |
| 6,703,632 | B1 | 3/2004 | Macklis et al. | |
| 7,057,194 | B2 | 6/2006 | Goldstein | |
| 7,276,716 | B1 | 10/2007 | Munro, III | |
| 7,303,334 | B2 * | 12/2007 | Cadwalader | A61B 6/4423 378/4 |
| 7,331,712 | B2 | 2/2008 | Fischer et al. | |
| 7,391,042 | B2 | 6/2008 | Goldstein | |
| 7,465,947 | B2 | 12/2008 | Magram | |
| 7,608,847 | B2 | 10/2009 | Rees | |
| 7,638,784 | B2 | 12/2009 | Fox et al. | |
| 7,829,873 | B2 | 11/2010 | Fox et al. | |
| 7,973,299 | B2 * | 7/2011 | Rees | A61B 6/107 250/516.1 |
| 8,143,607 | B2 | 3/2012 | Teodorescu | |
| 8,378,326 | B2 | 2/2013 | Hunt | |
| 8,399,871 | B2 | 3/2013 | Beyar et al. | |
| 8,439,564 | B2 | 5/2013 | Belson et al. | |
| 8,598,554 | B2 | 12/2013 | Rees | |
| 8,683,928 | B2 | 4/2014 | Anderson | |
| 8,716,687 | B2 | 5/2014 | Goldstein et al. | |
| 9,101,272 | B2 * | 8/2015 | O'Loughlin | A61B 6/032 |
| 9,349,492 | B1 | 5/2016 | Ganus | |
| D772,414 | S | 11/2016 | Ballsieper | |
| 9,655,571 | B2 | 5/2017 | Hunt | |
| 9,877,688 | B1 | 1/2018 | Colling | |
| 10,016,172 | B2 * | 7/2018 | Wilson | A61B 6/107 |
| 10,441,231 | B2 | 10/2019 | Wilson et al. | |
| D872,278 | S * | 1/2020 | Ballsieper | D24/158 |
| 10,548,795 | B2 | 2/2020 | Conner et al. | |
| 10,568,591 | B2 | 2/2020 | Egolf et al. | |
| 10,675,111 | B2 | 6/2020 | Goy et al. | |
| 10,856,819 | B2 | 12/2020 | Gordon | |
| 10,861,611 | B2 | 12/2020 | Gordon | |
| 10,912,526 | B1 * | 2/2021 | Baird | A61B 6/107 |
| 11,006,909 | B2 * | 5/2021 | Yifat | A61B 6/4441 |
| 11,076,819 | B2 | 8/2021 | Belson et al. | |
| 11,109,932 | B2 | 9/2021 | Goy et al. | |
| 11,191,495 | B2 | 12/2021 | Wilson et al. | |
| 11,219,566 | B2 | 1/2022 | Wilson et al. | |
| 11,517,271 | B2 * | 12/2022 | Achleitner | A61B 6/4441 |
| 11,660,056 | B2 | 5/2023 | Foster et al. | |
| 11,666,290 | B2 | 6/2023 | Wilson et al. | |
| 11,948,701 | B2 * | 4/2024 | Gordon | A61B 6/107 |
| 12,053,312 | B2 | 8/2024 | Wilson et al. | |
| 12,119,126 | B2 * | 10/2024 | Yifat | G21F 3/00 |
| 12,279,899 | B2 * | 4/2025 | Foster | G21F 3/00 |
| 2004/0045557 | A1 | 3/2004 | Lee et al. | |
| 2004/0188638 | A1 * | 9/2004 | Mossor | E02D 29/0258 250/515.1 |
| 2006/0124871 | A1 | 6/2006 | Ballsieper | |
| 2006/0156472 | A1 | 7/2006 | Ansel | |
| 2006/0251219 | A1 * | 11/2006 | Cadwalader | A61B 6/107 378/203 |
| 2008/0119722 | A1 * | 5/2008 | Swaney | A61B 6/488 128/846 |
| 2008/0164425 | A1 * | 7/2008 | Cadwalader | A61B 6/107 250/492.1 |
| 2010/0319713 | A1 | 12/2010 | Byers et al. | |
| 2011/0095209 | A1 | 4/2011 | Cadwalader et al. | |
| 2011/0174997 | A1 | 7/2011 | Rees | |
| 2011/0184278 | A1 | 7/2011 | Goff et al. | |
| 2012/0049093 | A1 | 3/2012 | Costea | |
| 2012/0132217 | A1 * | 5/2012 | Rees | A61B 6/4423 128/849 |
| 2012/0241652 | A1 | 9/2012 | Jeschke | |
| 2012/0256092 | A1 | 10/2012 | Zingerman | |
| 2013/0112899 | A1 | 5/2013 | Schulz et al. | |
| 2013/0320246 | A1 | 12/2013 | Beck | |
| 2014/0029720 | A1 | 1/2014 | Osherov et al. | |
| 2014/0048730 | A1 | 2/2014 | Niedzielski et al. | |
| 2014/0151584 | A1 | 6/2014 | Khandkar et al. | |
| 2015/0272519 | A1 | 10/2015 | Buchmeyer | |
| 2015/0335297 | A1 | 11/2015 | Mogul et al. | |
| 2016/0027540 | A1 | 1/2016 | Gordon et al. | |
| 2016/0029980 | A1 | 2/2016 | Osherov et al. | |
| 2016/0038365 | A1 | 2/2016 | Conner et al. | |
| 2016/0158082 | A1 * | 6/2016 | Gainor | A61G 7/05 |
| 2016/0220199 | A1 | 8/2016 | Gordon | |
| 2017/0027532 | A1 * | 2/2017 | Joshi | A61B 6/586 |
| 2018/0235555 | A1 * | 8/2018 | Shealy | A61B 6/00 |
| 2018/0301235 | A1 * | 10/2018 | Kawahara | A61B 6/4411 |
| 2019/0336088 | A1 | 11/2019 | Gordon | |
| 2020/0352528 | A1 | 11/2020 | Foster et al. | |
| 2021/0161484 | A1 * | 6/2021 | Wilson | A61B 6/107 |
| 2021/0280333 | A1 | 9/2021 | Marsh | |
| 2021/0401383 | A1 * | 12/2021 | Yadegari | A61G 13/124 |
| 2022/0218295 | A1 | 7/2022 | Foster et al. | |
| 2022/0233384 | A1 | 7/2022 | Yadegari et al. | |
| 2022/0262533 | A1 * | 8/2022 | Van De Geer | A61G 13/10 |
| 2023/0120289 | A1 * | 4/2023 | Wilson | A61B 6/107 378/203 |
| 2024/0099673 | A1 * | 3/2024 | Wilson | A61B 6/107 |
| 2025/0127466 | A1 * | 4/2025 | Wilson | A61B 6/107 |

FOREIGN PATENT DOCUMENTS

| | | | | |
|---|---|---|---|---|
| CA | 3098732 | A1 | 12/2019 | |
| CA | 3123289 | A1 | 12/2021 | |
| CN | 106618627 | A * | 5/2017 | A61B 6/107 |
| DE | 29706321 | U1 | 7/1997 | |
| DE | 102014215448 | B3 | 12/2015 | |
| DE | 102020206784 | A1 | 7/2021 | |
| EP | 1613217 | A1 | 1/2006 | |
| EP | 3932320 | A1 | 1/2022 | |
| GB | 1051979 | A | 12/1966 | |
| JP | S5336700 | U | 3/1978 | |
| JP | S63-68305 | U | 5/1988 | |
| JP | 2001120543 | A | 5/2001 | |
| JP | 2021106927 | A | 7/2021 | |
| JP | 2021115113 | A * | 8/2021 | |
| KR | 101081895 | B1 | 11/2011 | |
| WO | 2014078553 | A1 | 5/2014 | |
| WO | 2015012906 | A1 | 1/2015 | |
| WO | 2015018240 | A1 | 2/2015 | |
| WO | 2017116530 | A2 | 7/2017 | |
| WO | 2017218871 | A1 | 12/2017 | |
| WO | 2019227210 | A1 | 12/2019 | |
| WO | 2021168219 | A1 | 8/2021 | |

OTHER PUBLICATIONS

English machine translation for JP-2021115113-A (Year: 2021).*

International Patent Application No. PCT/US2022/047164, International Search Report and Written Opinion mailed Apr. 24, 2023, 20 pages.

PCT Partial International Search Report dated Feb. 15, 2023 for International Application No. PCT/US2022/047164, 7 pages.

Aadco Medical, Inc. "Innovative Quality Solutions for Medical Imaging" Brochure published Oct. 10, 2015, pp. 108.

Rampart, "L148 Lead-Free Table Draping for Cath Labs", Downloaded from: https://www.rampartic.com/1148-table-mounted-cath-lab-radiation-shielding, Downloaded Jun. 21, 2024, pp. 3.

European Patent Office, "Extended European Search Report", From Application No. 25150196.1, dated Apr. 22, 2025, pp. 9.

Fetterly et al., "Effective Use of Radiation Shields to Minimize Operator Dose During Invasive Cardiology Procedures", JACC:

(56) References Cited

OTHER PUBLICATIONS

Cardiovascular Interventions, vol. 4, No. 10, Published May 25, 2011, pp. 7.

European Patent Office, “Extended European Search Report”, From Application No. 25150181.3, dated Feb. 20, 2025, pp. 12.

* cited by examiner

FIG. 6A
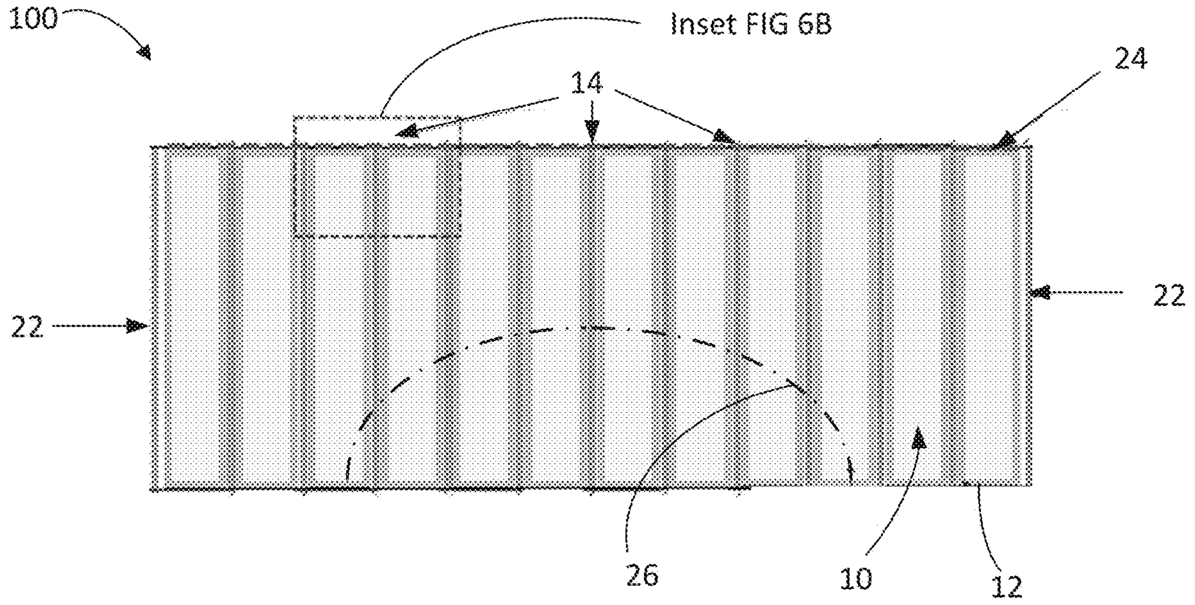
FIG. 6B
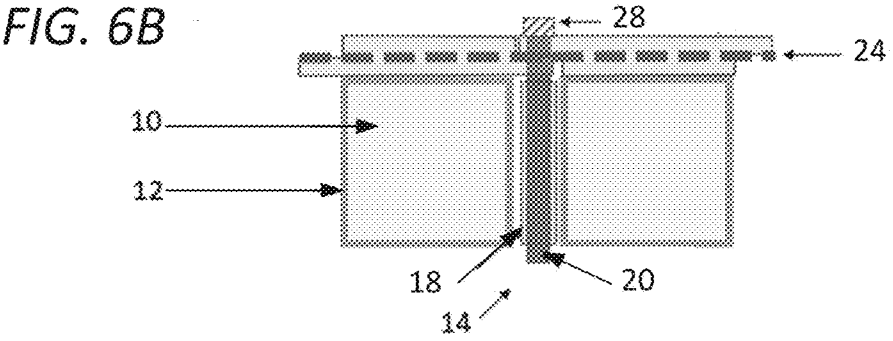
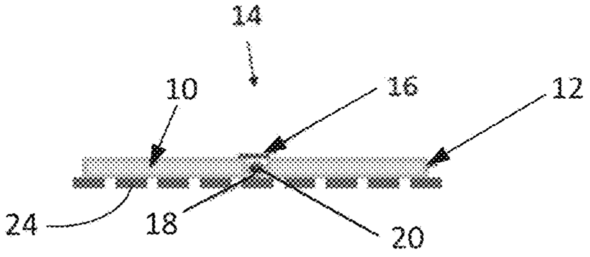
FIG. 6C

FIG. 8A
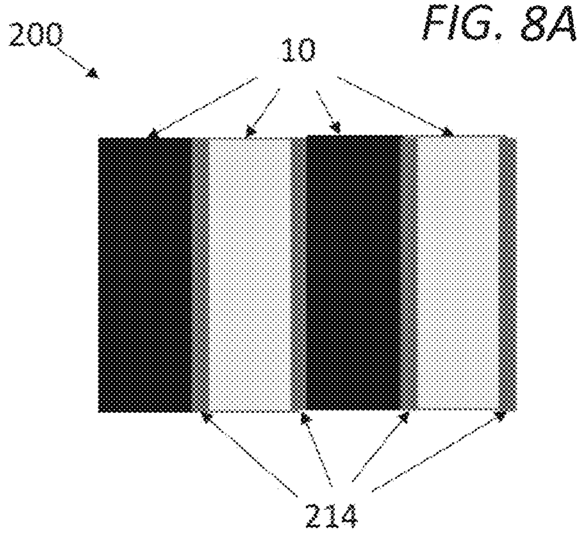
FIG. 8B
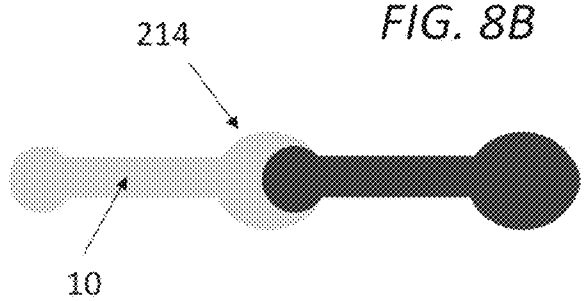
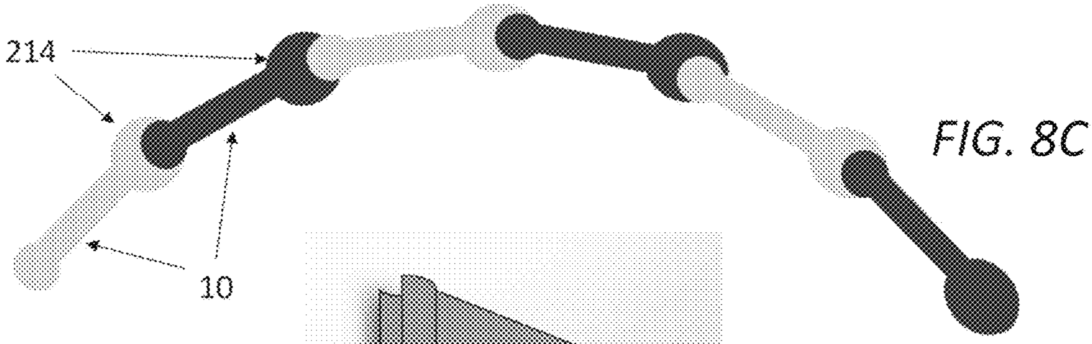
FIG. 8C
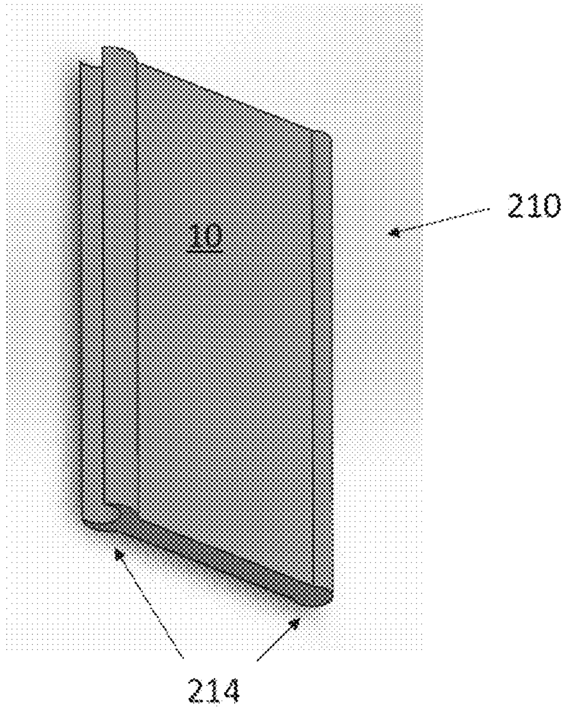
FIG. 8D

DEVICES TO REDUCE RADIATION EXPOSURE

RELATED APPLICATIONS

This application claims priority to U.S. Provisional Patent Application No. 63/270,309, filed Oct. 21, 2021, and to U.S. Provisional Patent Application No. 63/341,894, filed May 13, 2022, the entire contents of both of which are incorporated herein by reference.

TECHNICAL FIELD

This disclosure relates generally to shielding devices and systems for reducing exposure to radiation to hospital and medical staff during a variety of medical imaging procedures.

BACKGROUND

Healthcare workers in hospital or clinic x-ray laboratories are often exposed to radiation, including scatter radiation (or secondary radiation) emanating from patients undergoing x-ray imaging studies and x-ray guided treatment, such as angiograms, intravascular stenting and transcatheter heart valve therapy. Shielding to absorb x-ray photons is used to protect workers from this scatter radiation. A common form of shielding is an apron worn by the user that contains a shielding material such as lead or a polymer loaded with shielding elements such as antimony, bismuth, and tin. These aprons may not cover the entire body, leaving exposed body parts subject to irradiation. Other forms of shielding (e.g., radiation blocking eyeglasses, shin guards, arm guards, skull caps, etc.) are sometimes worn to cover sensitive areas of the body not shielded by the apron, but they may not be particularly effective. Additionally, the aprons and similar worn shielding can be heavy, which may lead to fatigue, injury, and/or other orthopedic problems for the user.

During x-ray imaging procedures, the x-ray table (or procedure table) is frequently moved to view different parts of a patient's body. In addition, the x-ray tube and detector are usually mounted on opposite sides of a C-arm gantry, where the gantry can be rotated in up to 3 planes. The movement of equipment can pose challenges to and constraints on the use of certain types of external shields.

Shields placed on the floor may limit operator movement around the table. Shields over a patient may only be effective in blocking radiation scattered above the table, where a minority of x-ray scatter radiation exists. Shields mounted on the x-ray table can potentially interfere with x-ray gantry motion and/or add significant weight to the x-ray table. X-ray tables may, for example, have weight limits, and the addition of heavy shielding can limit the weight of patients that can be imaged safely on the table. In addition to the practical mechanical considerations affecting the use of existing shielding systems, there are no known methods for ensuring that the system is properly positioned or that radiation is not leaking from the system.

Radiation shielding used in hospital x-ray laboratories can be divided into shielding that is clear and shielding that is opaque (or non-transparent). Clear shielding material is used so that the healthcare personnel can view the patient or surroundings during x-ray imaging, while opaque shielding is used when such visualization is not as important. One problem with the existing clear radiation shielding is that the clear shields are composed of rigid acrylic or glass material loaded with radiation blocking elements, such as lead oxide.

The lack of flexibility of materials commonly used in the manufacture of clear or transparent shielding results in large planar shields that are cumbersome to use, do not adequately surround the user, and may limit the mobility of the x-ray gantry as it is moved and/or angled to obtain oblique x-ray projections of the patient, for example.

To compensate for this lack of flexibility, the rigid transparent shields often have flexible non-transparent flaps attached to the shield, often to the bottom of the shield to approximate the shield to the irregular contour of a patient's body. The flexible material, however, does not allow the operator to view the patient, and its use is therefore usually confined to the areas where viewing the patient is less important.

Additionally, shielding is typically arranged around the table in the x-ray laboratory based on where rails are mounted to the lab table. In most imaging labs, the rails reside on the table towards the caudal end of the patient, as the rails are often metallic and will interfere with x-ray imaging if they reside within the field of view. The use of existing rails on which to mount and/or support shielding may not provide the best positioning of shielding to protect the laboratory staff from the effects of scatter radiation.

One attempt to remedy this situation is to mount a component to the table in the position where an operator intends to stand for a procedure. This means that the table must be assembled in a very particular way, a challenge when the types of procedures and the position of the operator may vary from case-to-case, or even during a case.

There is a need for shielding systems and devices that protect hospital workers from exposure to scatter radiation, allowing them to function wearing typical hospital attire without relying entirely on wearing a lead apron or other personal protective equipment. There is a further need to assess or ensure proper placement of shielding and/or detect when radiation is not being blocked or exceeds certain levels.

SUMMARY

In general, this disclosure is directed to an apparatus and method that may be useful in reducing exposure to radiation. This disclosure describes a system and/or method for reducing the exposure of workers (e.g., physicians, nurses, technicians, lab staff, etc.) to scatter radiation that may arise during the performance of certain medical imaging procedures.

In certain embodiments, a shielding system may include a belt or belt portion, a radiation shield portion, and one or more engagements sensors configured to detect engagement (e.g., to detect a level or degree of engagement) between the belt portion and the shield portion of the shielding system. The belt portion provides a radiation shielding seal over the surface of the patient and surrounding support structures (such as appliances to position the patient, the x-ray table, and other structures on or around the x-ray table). The belt may also provide a means to connect the irregular surfaces of the patient and procedure field with the regular structure of the surrounding x-ray shielding, enhancing the shielding of x-rays. Moreover, the shielding belt portion can be sterilized and applied directly to the procedure field to conform to the irregular surfaces, while allowing the shielding around the patient to mate with the shielding belt portion. In certain embodiments, a shielding system may further include radiation sensors (e.g., radiation detection sensors) disposed near the procedure table, which may be configured to detect and/or indicate the presence of radiation, or levels of radiation in excess of a predetermined threshold level, for example. In some embodiments, a method of using a shielding system may comprise the following steps: (a) placing a belt portion across a portion of a patient on a procedure table; (b) releasably engaging a shield portion with the belt portion along a junction; and (c) performing an imaging procedure.

In certain embodiments, a flexible radiation shielding system is described, such as a multi-articulated shielding system. A multi-articulated shielding system may comprise a number of shielding elements hingedly or pivotably coupled together, which may allow a user to bend the shielding system (e.g., at the couplings or joints between adjacent shielding elements, for example) into various shapes, while providing a suitable level of radiation shielding protection to workers. In some embodiments, the multi-articulated shielding system may comprise shielding elements that are, for example, translucent, transparent, clear, etc., to enable workers to view a patient and/or other objects through the shielding elements of the flexible radiation shielding system.

In some embodiments, a flexible radiation shielding system according to this disclosure may comprise: two or more shielding elements formed of a radiation blocking material, such as leaded glass or acrylic (e.g., clear, transparent, translucent, etc.); at least one hinged connection between two shielding elements hingedly coupling the elements to each other; and a mechanism or means for blocking radiation at an interface between the elements when the elements are hingedly rotated or pivoted relative to one another such that the shield assumes a shape, such as a convex shape, or a concave shape, or a combination thereof. In some embodiments, the shielding elements may have an optional shielding frame disposed around at least a portion of the shielding element. A method of supporting or suspending a flexible element shield system is also described according to some embodiments of this disclosure.

In some embodiments, a flexible element shield according to this disclosure may comprise two or more radiation blocking or shielding elements, wherein at least some of the elements comprise a clear surface with a hinge element integral to the shielding element, such that multiple shielding elements can be assembled together to form a flexible shield.

In some embodiments, a shielding array support system according to this disclosure may be used to removably position radiation shielding around a medical procedure table based on the needs of the procedure in order to provide radiation protection for those working in a procedure room, for example. The shielding array system may comprise a base structure configured to enable attachment thereto of other shielding components and/or related accessories. Some shielding components of such a system may be configured to provide radiation protection to portions of the patient as well.

The details of one or more examples are set forth in the accompanying drawings and the description below. Other features, objects, and advantages will be apparent from the description and drawings, and from the claims.

BRIEF DESCRIPTION OF DRAWINGS

FIG. 6A is a front view of a flexible radiation shielding system according to some embodiments of this disclosure;

FIG. 6B is an enlarged front cross-sectional view of a portion of a flexible radiation shielding system (inset from FIG. 6A) according to some embodiments of this disclosure;

FIG. 6C is an enlarged top plan view of a portion of a flexible radiation shielding system according to some embodiments of this disclosure;

FIG. 8A is a front view of a flexible radiation shielding system according to some alternate embodiments of this disclosure;

FIGS. 8B and 8C are enlarged top views of a hinge joint arrangement for a flexible radiation shielding system according to some alternate embodiments of this disclosure;

FIG. 8D is a lower perspective view of an individual shielding pane having the hinge joint arrangement of FIGS. 8A-8C;

DETAILED DESCRIPTION

A shielding device, system, or method according to some embodiments disclosed herein may provide protection to a worker (e.g., a healthcare worker, hospital staff, etc.) and/or a patient from scatter radiation that may result during certain medical imaging procedures. Such a shielding device or system may thereby permit such workers to function without the need for wearing certain forms of shielding, such as a shielding apron. In some embodiments, a shielding device or system may be configured to move with movement of the procedure table (e.g., x-ray table) and/or workflow during a procedure. In some embodiments, the shielding device may add minimal weight to the x-ray table. In certain embodiments, the shielding device may provide an indication and/or a feedback loop to a worker or an operator, for example, indicating that the shielding device has been properly positioned or engaged, and/or indicating to a worker whether the radiation field is above, at, or below a predetermined level, or simply indicating the level of radiation (possibly through the use of audible and/or visible indicia, for example).

Figure 1A:
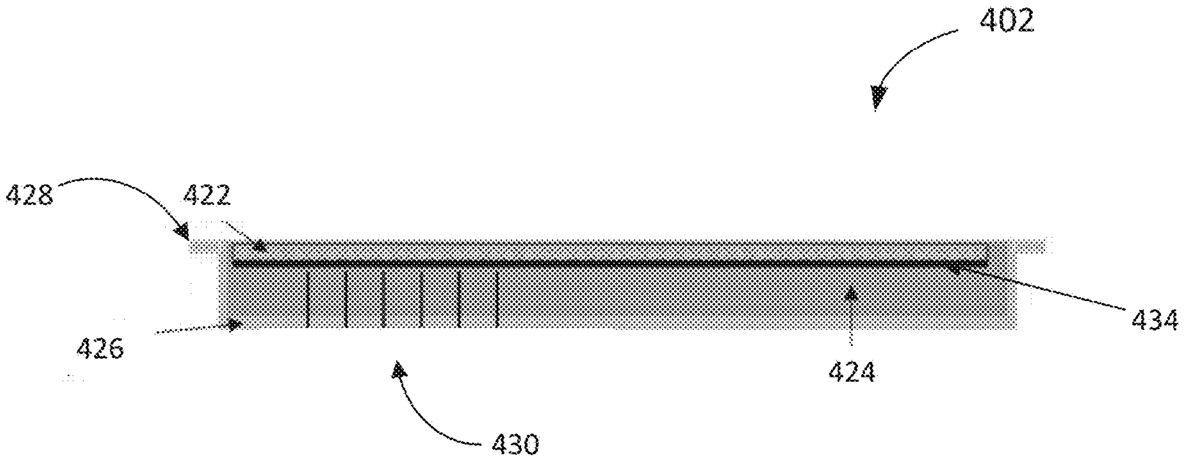
FIG. 1A is a schematic top view of an embodiment of a radiation shielding belt portion with slits to enable the radiation shielding belt portion to conform to at least a portion of a patient.
Figure 1B:
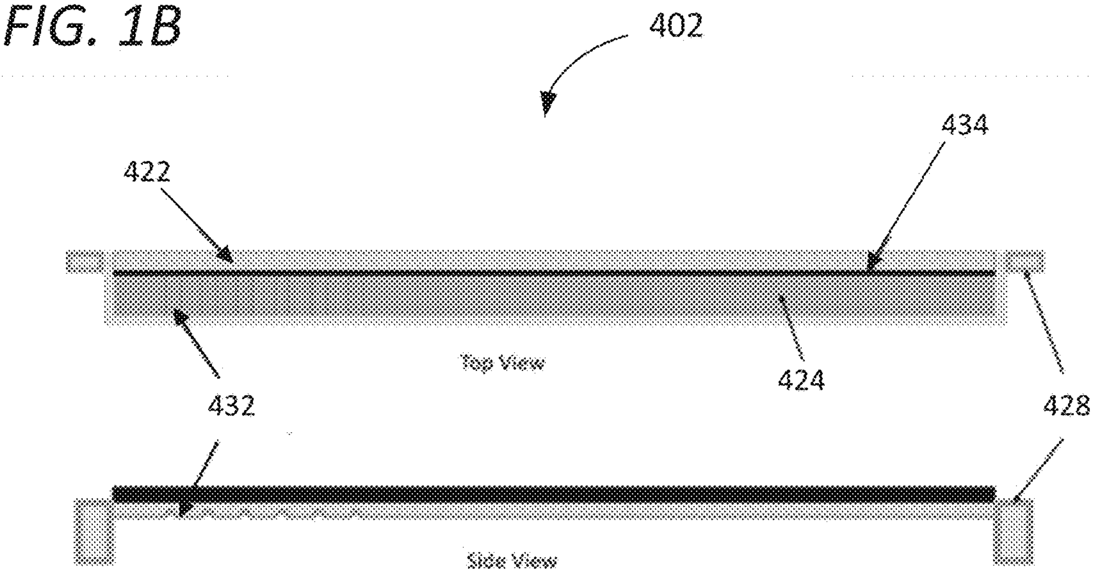
FIG. 1B includes a schematic top view and a schematic cross-sectional view of an embodiment of a radiation shielding belt portion with undulations formed therein to enable the radiation shielding belt portion to conform to at least a portion of a patient.

A radiation shielding device/system 400 as described herein may include a radiation shielding belt portion 402 (as shown in FIGS. 1A and 1B) configured to be placed over, around or across at least a portion of a patient 500 positioned on an imaging procedure table. The belt portion 402 may be deformable to conform to a surface of the patient and may further have a configuration adapted to releasably engage or mate with a radiation shield portion 408 (as shown in FIGS. 2 and FIGS. 3A-3C). The belt portion 402 and the shield portion 408 comprise materials having radiation-shielding properties. In some embodiments, the radiation shielding belt portion 402 may be designed to be a single-use, disposable component of a radiation shielding device/system 400. In some further embodiments, the radiation shielding belt portion 402 may be provided in sterile packaging to be a single-use, disposable component used with a radiation shielding device/system 400 for a single procedure, or for a single patient, and then discarded/disposed of, for example.

Figure 2:
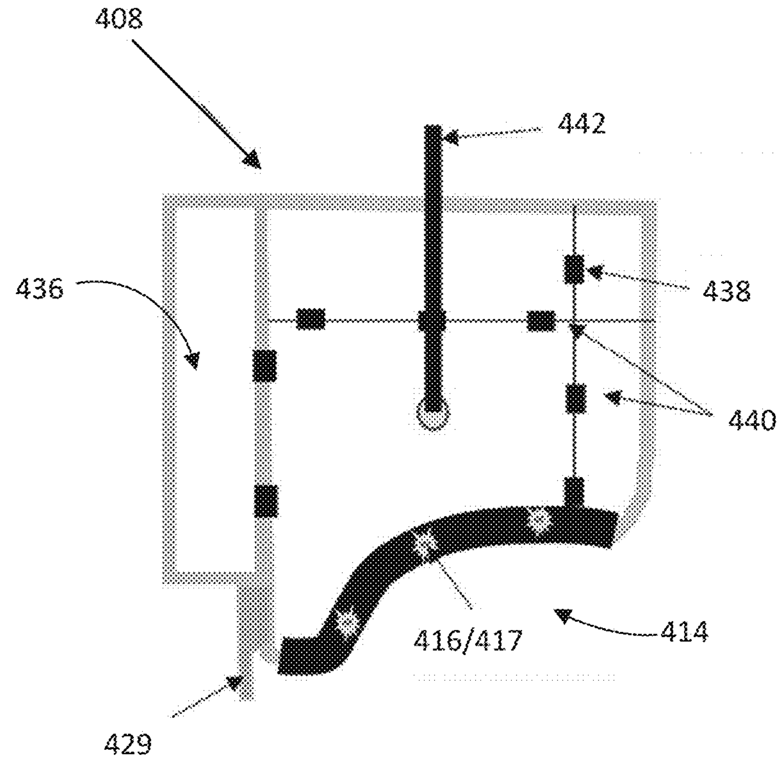
FIG. 2 is a schematic front view of an embodiment of a radiation shield portion configured to engage with a radiation shielding belt portion.

The radiation shield portion 408 may be configured, in some embodiments, to be suspended from a ceiling, or from a floor mounted cantilever boom, or suspended from an attachment to a procedure table 502, or from some other instrument affixed to the x-ray/procedure table 502 and/or mattress 506 (see FIGS. 3B, 4B, and 5B), for example. The radiation shield portion 408 (e.g., as shown in FIG. 2) is configured to releasably or reversibly engage or mate with the radiation shielding belt portion 402 to form a radiation barrier (e.g., to prevent leakage of scatter radiation) at or along a junction 412 formed between the radiation shielding belt portion 402 and the radiation shield portion 408 (see FIGS. 3A-3C and FIGS. 4A-4B). The shield portion 408 may be configured to extend upwardly from the patient when the belt portion 402 is engaged with the shield portion 408. The shield portion 408 may comprise a table attachment 429 for releasably coupling the shield portion to the procedure table, according to some embodiments.

In some embodiments, a contact sensor system 414 comprising one or more contact sensors or engagement sensors 416 disposed along the junction 412 between the radiation shielding belt portion 402 and the radiation shield portion 408. The engagement sensors 416 may be configured to sense and/or provide an indication of (e.g., display) the presence or absence of (and optionally, the degree or extent of) operable engagement between the belt portion 402 and the shield portion 408 at one or more locations along the junction 412 between the belt portion 402 and the shield portion 408. In some variations, contact/engagement sensors 416 may also include contact sensor lights 417 to provide a visual indication of the operable engagement (e.g., green=engaged, red=misaligned) at the junction 412 or at another position in the procedure room.

Figure 3A:
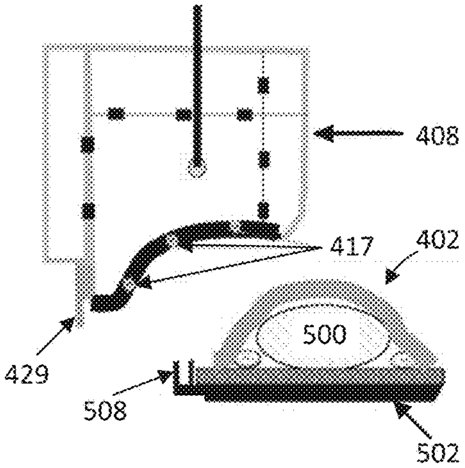
FIGS. 3A-3C are schematic views showing a radiation shielding system comprising a belt portion and a shield portion configured to be disposed in operable engagement with each other and, optionally, an embodiment of a shield portion configured for attachment to a procedure table.
Figure 3B:
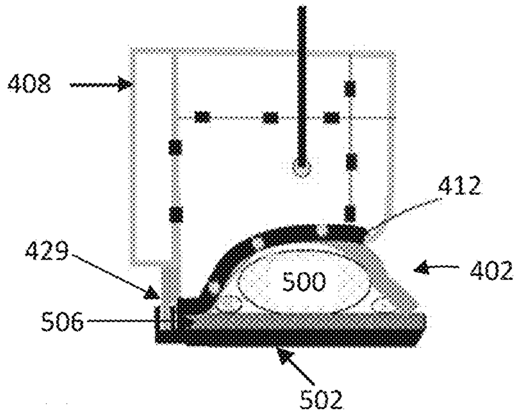
Figure 4A:
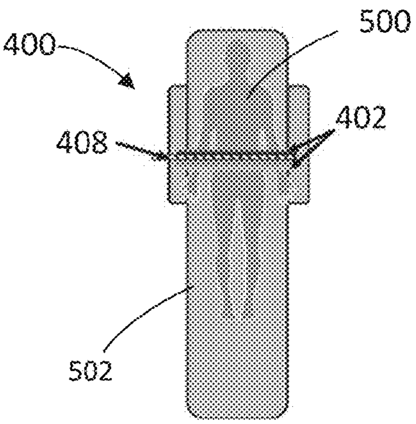
FIGS. 4A and 4B are schematic representations (top view and side view, respectively) of an embodiment of a radiation shielding system including a belt portion and a shield portion in operable engagement.
Figure 4B:
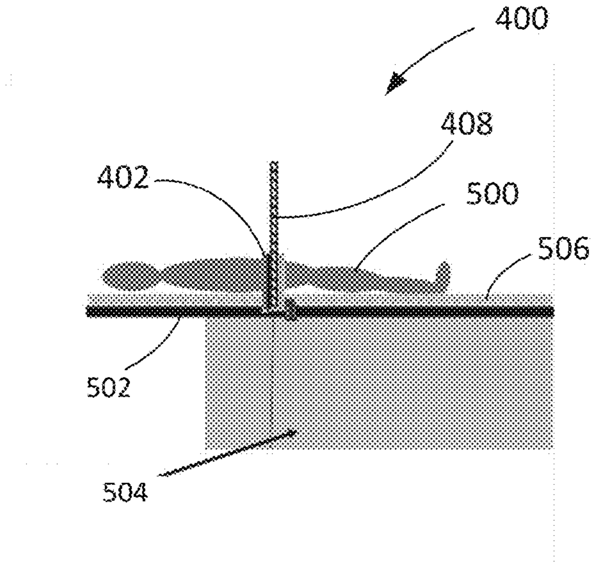

In the embodiment shown in FIGS. 3A and 3B, a reversible or releasable engagement may be provided between the radiation shield portion 408 and the procedure table 502 (or to an object affixed to the procedure table 502, or to an object on which the patient lies, such as mattress 506), thereby allowing the radiation shield portion 408 to move with movement of the procedure table 502. This may be provided in some cases by the use of a table attachment 429 formed in the radiation shield portion 408 and configured to mate and/or engage with a receiver 508, which may be formed in procedure table 502, or in belt portion 402, or in both (e.g., in a nested configuration, for example).

Figure 5A:
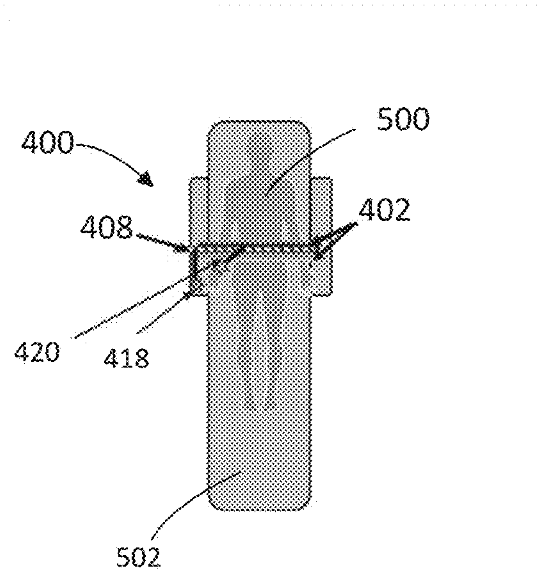
FIGS. 5A and 5B are schematic representations (top view and side view, respectively) of an embodiment of a radiation shielding system including a belt portion and a shield portion in operable engagement, and having radiation detection sensors arranged to detect and display radiation levels and/or the presence of radiation leakage around or through the radiation shielding system.
Figure 5B:
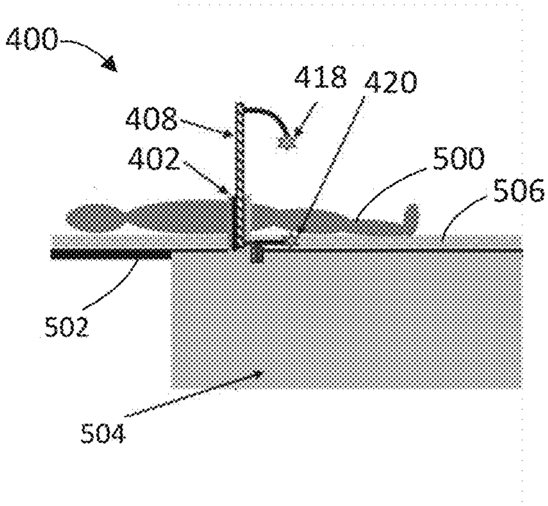

In some embodiments, one or more radiation detection sensors 418 may be disposed proximate to a procedure table 502, or affixed to the procedure table 502 itself, or to one or more object(s) affixed to the procedure table 502, or to a shielding device, for example, where the one or more radiation detection sensors 418 may measure an x-ray radiation level, for example, and are configured to indicate a level of x-ray radiation intensity at or near the radiation detection sensor(s) 418 (see FIGS. 5A and 5B). For example, an x-ray shielding system 400 may optionally include an x-ray detection system 420 comprising one or more radiation detection sensors 418 to help ensure that a worker or operator is not being exposed to radiation levels above a certain predetermined or predefined limit. In some alternate embodiments, the x-ray detection system 420 may provide a real-time warning, for example, via a numerical display, or via an audible sound or vibration proportional to the level of radiation present, or a light or graphic signal proportional to the radiation level, etc. In some alternate embodiments, the x-ray detection system 420 may indicate a real-time warning that a certain level of radiation is being exceeded, such as by using a colored light indication (e.g., red, yellow, green, corresponding to varying levels of radiation intensity), a sound, a vibration, or other suitable indications warning a worker that a specified radiation level has been exceeded. In some embodiments, radiation detection sensors 418 may include the ability to change the color or light intensity of a display to provide a visual indication, and may be adjustable or programmable to vary the setpoints as needed. In some alternate embodiments, the x-ray detection system 420 may include a feedback control mechanism in which the real-time level of sensed radiation is fed back to the x-ray system, possibly resulting in a pause or termination of the x-ray generation, or a reduction in x-ray dose levels or intensity, or in some other action to reduce the radiation levels detected by system 420 to a safe level, for example.

A shielding system 400 according to some embodiments may be used in conjunction with the use of a table radiation shield 504 (see FIGS. 4A, 4B, 5A, and 5B, for example) that hangs from or is supported by the procedure table 502, or from a device mounted on or to the table 502 or mattress 506, etc., typically used to provide shielding from radiation below the table 502. Similarly, a floor mounted shield, with or without attachment to the procedure table 502 or pedestal, or a similar shield suspended from a ceiling, for example, could be used to provide protection from radiation below the table 502.

Radiation Shielding Belt Portion

Figure 1C:
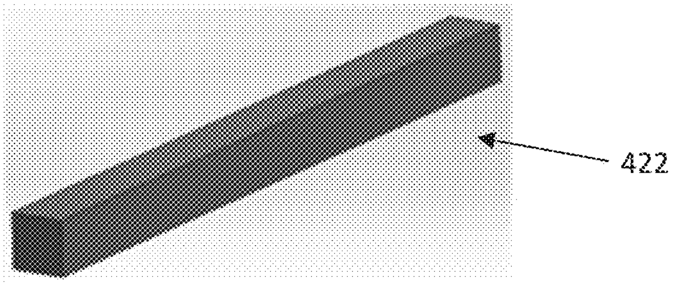
FIGS. 1C-1E are perspective views of exemplary components of a radiation shielding belt portion according to some embodiments of this disclosure.
Figure 1D:
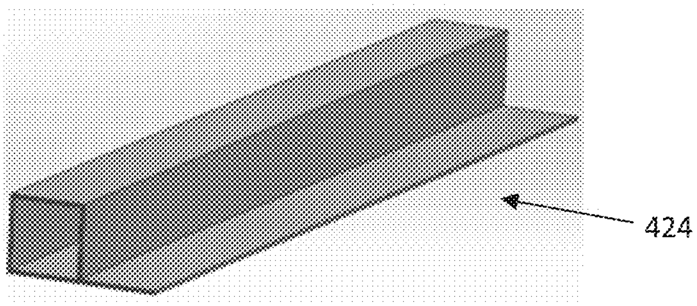
Figure 1E:
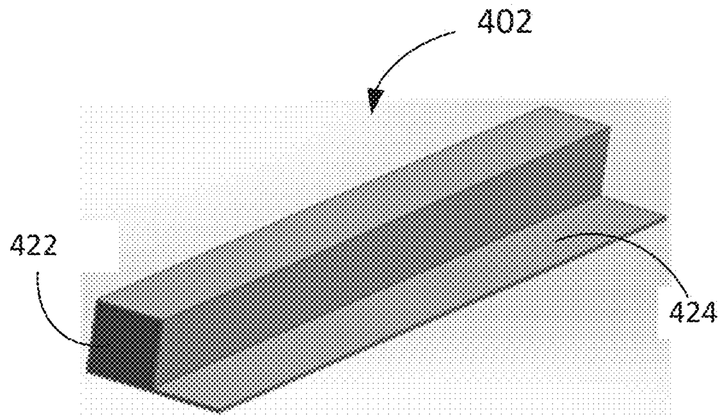

FIGS. 1A and 1B show exemplary radiation shielding belt portions 402, according to various embodiments of this disclosure. FIG. 1A, for example, is a top view of a radiation shielding belt portion 402 comprising a radiation shielding material 424, foam 422 or other material adapted to provide a three-dimensional shape to the belt portion 402, and a covering 426. The belt portion 402 is intended to be placed over or across a portion of the patient, typically over and/or across the waist or lower abdomen of the patient. Radiation shielding material 424 may comprise a radiation blocking rubber material (e.g., a rubber filled with materials such as tin, antimony, bismuth, etc.), for example. Foam 422 provides a vertical dimension or height to the belt portion 420 to facilitate engagement with the radiation shield portion 408, for example. Foam 422 may also provide a flexible aspect to facilitate conforming placement or engagement with radiation shield portion 408 and against a surface of the patient. In some embodiments, radiation shielding material 424 may be formed around foam 422 and may also extend horizontally from foam 422. This configuration is best illustrated in FIGS. 1C-1E.

Figure 3C:
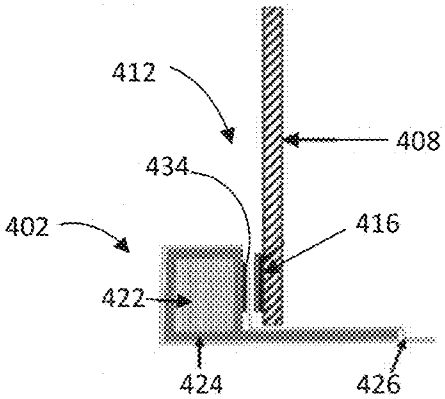

The belt portion 402 may have a vertical dimension (e.g., a portion having a height that extends upwardly away from the procedure table 502 when positioned across a portion of a patient, for example, the vertical height of the foam 422 shown in FIG. 3C) sufficient to facilitate engagement with the radiation shield portion 408 and prevent x-ray photon leakage along a junction 412 to be formed between the belt portion 402 and the radiation shield portion 408. In some embodiments, the belt portion 402 abuts the radiation shield portion 408 in a manner similar to the that of a door and a doorjamb. That is, the belt portion 402 may comprise an abutting surface to facilitate releasable engagement with the shield portion 408 along the junction 412 between the belt portion 402 and the shield portion 408.

The radiation shielding belt portion 402 may be manufactured to be used as a sterile or non-sterile device or component of the shielding system. A non-sterile belt portion 402 may, for example, be placed under a sterile patient drape during use, whereas a sterile belt portion 402 could be placed in the sterile field over a patient sterile drape during use, for example. The belt portion 402, in certain embodiments, may be configured to be attached to the procedure table 502 (or another device on the procedure table 502), or to a sterile drape over a patient using one or more of a number of suitable engagement or mating methods (such as magnetic elements, a latch, a hook and loop strip (Velcro), or an adhesive). For example, one or more magnetic elements may be disposed along the junction 412 between the belt portion 402 and the shield portion 408 in certain embodiments. Optional slits 430 and/or undulations 432 formed in portions of the belt portion 402, or in the shielding material 424 thereof, may provide additional conformability to a patient's body, as shown in FIGS. 1A and 1B. For example, a plurality of slits 430 and/or a plurality of undulations 432 formed in belt portion 402 may facilitate conforming of the belt portion 402 to an upper surface of a patient in some embodiments. The belt portion 402 may be configured to entirely cross or encompass a patient or procedure table, or in some cases may be configured to extend at least partially across an upward-facing surface of a patient (such as the right half of the abdominal area), or to extend at least partially across a width of the procedure table, according to some embodiments. The radiation shielding belt portion 402 may manufactured to be used as a sterile component of the shielding system; for example, radiation shielding belt portion 402 may be provided in sterile packaging to be a single-use, disposable component used with a radiation shielding device/system 400 for a single procedure, or for a single patient, and then discarded/disposed of, for example.

FIGS. 1A and 1B show table attachments 428, which may extend outwardly and/or downwardly from at least one end of the belt portion 402 (e.g., FIGS. 1A and 1B show an embodiment in which table attachments 428 extend from both ends of belt portion 402, for example). In some embodiments, at least one table attachment 428 may be configured to engage and/or mate with a slot or other engagement mechanism of procedure table 502; this may, in some cases, facilitate maintaining a somewhat fixed orientation or geometric relationship between portions of the shielding system 400 and the procedure table 502 in order to maintain such relative orientation during movement of the procedure table 502 during various imaging operations for example. FIGS. 1A and 1B also show an embodiment of belt portion 402 having a ferromagnetic material 434 disposed along a surface of the belt portion 402. Ferromagnetic material 434 may be used in some embodiments to facilitate and/or enhance a positive engagement or mating between belt portion 402 and shielding portion 408 of shielding system 400. (FIG. 3C is a cross-sectional view showing details of a potential arrangement of ferromagnetic material 434 disposed along a vertically-oriented surface of foam 422 of belt portion 402. As noted, this arrangement may facilitate forming a positive engagement or mating between belt portion 402 and shield portion 408.

In an alternative configuration, the radiation shielding belt portion 402 may include a bladder disposed along a length (or along a longitudinal axis) of the belt. In such an embodiment, the bladder may be filled with a compressible material such as air, fluid or foam. This may allow the bladder to form a seal with or against a radiation shield portion 408 positioned over, across, or adjacent the belt portion 402, thereby creating a radiation barrier or block. The belt portion 402 may be covered in a sterile barrier material, for example, to facilitate use on the sterile field.

In some alternate embodiments, radiation shielding belt portion 402 may be formed or constructed in other configurations that may provide additional flexibility in the belt to conform to the shape of the radiation shield portion 408 and/or the patient. The radiation shielding belt portion 402 may help block or fill any gaps that may otherwise form or arise between a lower portion of the radiation shield portion 408 and the body of the patient. Accordingly, the radiation shielding belt portion 402 may be configured to have a generally vertical portion or height extending upwardly from a contour of the patient's body that may facilitate filling any such gaps between the shield portion 408 and the patient.

Figure 1F:
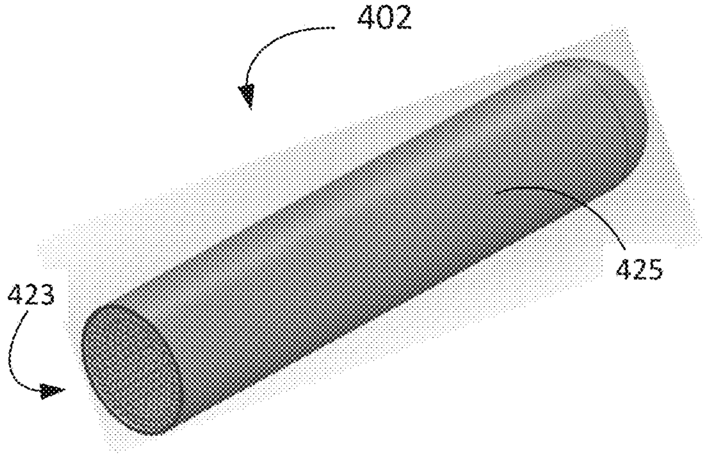
FIG. 1F is a perspective view of alternate components of a radiation shielding belt portion according to an alternate embodiment of this disclosure.

An example of a radiation shielding belt portion 402 according to some alternate embodiments is depicted in FIG. 1F. For example, FIG. 1F is a cut-away perspective view of a radiation shielding belt portion 402 comprising an elongate tube 425 filled with radiation-blocking fill particles 423. Elongate tube 425 may comprise a flexible tube, or other similar elongate shape, which may be formed of a fabric covering, for example, and filled with a radiation-blocking material that is non-continuous; that is, the radiation-blocking material may comprise a plurality of fill particles 423, for example. These radiation-blocking fill particles 423 may take the form of small pieces of cut foam, or beads made of glass, plastic, foam or similar materials. These beads may be round, elongate, cylindrical, square or any shape that allows for relative motion between the particles when the flexible tube 425 in which such particles (e.g., beads) are housed is flexed or shaped. In preferred embodiments, the relative motion between such radiation-blocking fill particles may resemble fluidic motion such that the flexible tube readily conforms to the shape of its surrounding environment.

These beads or other fill components 423 may be formed of and/or loaded with radiation-blocking materials during their manufacture. Suitable radiation-blocking materials may include materials such as lead, tin, antimony, barium, bismuth or other materials that attenuate x-ray radiation. The fill particles or beads 423 may also be coated with such radiation-blocking materials after manufacture. To provide the desired levels of radiation-blocking protection, for example, the radiation-blocking beads or fill particles 423 used in such an embodiment of belt portion 402 may be configured to provide bulk radiation attenuation properties that meet the requirements of the full system for lead equivalency. As examples, 0.5 mm lead equivalent and 1.0 mm lead equivalent are common goals or targets for x-ray shielding levels, although lower and higher levels of lead equivalency (e.g., between 0 mm and 0.5 mm lead equivalency, and greater than 1.0 mm lead equivalency) may also be envisioned according to various embodiments of this disclosure.

In another alternate embodiment of a radiation shielding belt portion 402, the "beanbag" fill particles 423 may be enclosed or contained by a flexible sheet or layer of radiation-blocking material. This radiation-blocking material may be malleable to provide the desired level of shape flexibility of the overall beanbag configuration, while continuing to provide the desired level of radiation protection.

The elongate tube 425 (for containing or housing the radiation-blocking fill particles 423) may itself be constructed of a fabric, an extruded polymer, or other material appropriate for use in medical device applications, for example. The elongate tube 425 of the radiation shielding belt portion 402 will be used in the sterile field during a medical procedure, and therefore should be constructed of a material that can be sterilized in advance of a procedure, or that can be inserted into a sterile bag or sterile barrier to prevent it from contaminating the sterile field, or which is manufactured and packaged as a sterile, single-use, disposable component of a shielding system, as possible examples.

As noted above, FIG. 1F is a cut-away perspective view of a radiation shielding belt portion 402 comprising an elongate tube 425 filled with radiation-blocking fill particles 423 that move relative to each other in a manner similar to the beads or beans of a typical "beanbag." The elongate tube 425 in this particular embodiment may be filled with fill particles 423 in a manner such that the belt portion 402 cannot dimensionally flatten below a specified thickness in any direction; this may, for example, help avoid a reduction in the x-ray attenuation properties of the belt portion 402 below a minimum radiation protection threshold. Such a feature may also provide a minimum height of the belt portion 402 to thereby maintain its ability to physically fill any gaps in shielding that may otherwise present themselves between the radiation shield portion 408 and the patient during imaging procedures, for example.

Radiation Shield Portion

A radiation shield (or shield portion 408) adapted to be positioned above a patient during use is configured to mate with a radiation shielding belt portion 402 conformingly disposed around a patient positioned on a procedure table 502, as shown in FIG. 2. The shield portion 408 may be formed of a transparent acrylic material, for example, with embedded shielding elements (such as lead oxide). The shield portion 408 may further have optional, additional components attached thereto, such as a handle to facilitate movement, a frame (or portion of a frame) to house sensors or other elements and to protect from damage, and a suspension apparatus to suspend the shield from an arm 442, or from a ceiling, floor mount, procedure table 502, or from an object affixed to the procedure table 502. The shield portion 408, or an attachment to the shield portion 408, may be releasably and/or reversibly mounted or coupled to the procedure table 502, or to a structure attached to the procedure table 502, allowing the shield portion 408 to move in conjunction with movements of the procedure table 502 during imaging procedures, for example, as shown in FIGS. 3A-3B and 4A-B. The shield portion 408, for example, may hang from an arm attached to the ceiling, or from struts within the ceiling or wall, or from a floor mounted cantilever mount.

The radiation shield portion 408 may be optionally configured with one or more pivot points 440 using a hinge mechanism 438, for example, as shown in FIG. 2. In one such embodiment, the edge of the hinged pieces has a step ledge such that bending the hinge out from a 0-degree-angle position will still provide a barrier to x-ray photon penetration. In addition, testing has shown that adding resistance to pivoting the hinges leads the operator to have more control in shaping the flexible shield. Additional mechanisms to allow the operator to form the shield into an arc by pulling or pushing one panel (e.g., panel 436) are the inclusion of a flexible structure between the panels (such as a flexible gooseneck tube), levels between panels to coordinate movements, and other mechanisms.

In some optional embodiments, a radiation shield portion 408 may further include an attachment, for example, the "Table attachment" 429 as shown in FIG. 2. In some embodiments, the attachment 429 is provided to the table itself, or to an object mounted on the table, such as a carbon fiber sled, an attached mattress, or a bracket affixed to the table or table rail. In some embodiments, a radiation shield portion 408 may include any of a number of mounts to the procedure table 502, or to a fixture on the procedure table 502, including a clamp, a bayonet attachment, a tongue and slot attachment, a magnetic attachment, a hook and loop attachment, and others as would be readily apparent to one of ordinary skill in the art.

The Table attachment 429 may also contain a sensor to detect table position and movement. For example, a sensor to detect up and down movement of the table may be connected to a mechanism to automatically move shielding around the patient up and down to match the table movement. Similarly, a sensor or sensors to detect side-to-side movement of the table or patient position can be connected to a motorized system to provide similar movement of the shielding system.

Releasable Engagement at Junction Between Belt and Shield Portions

A reversible and/or releasable engagement device or mechanism may be provided at or along the junction 412 between the radiation shield portion 408 and the belt portion 402. In one embodiment, such a releasable engagement element may aid in the mating of the belt portion 402 to the shield portion 408. As examples, one or more magnetic elements (for example, where there is a ferric element in either the shield's lower side or frame, or in a shield-facing side of the belt), with one or more corresponding magnetic elements on the opposing shield or belt), one or more hook and loop fasteners or fastening strips (e.g., Velcro), a latch, or an adhesive.

A proximity sensor system may be employed according to some embodiments to detect the presence (or lack thereof) of a connection between the radiation shield portion 408 and the belt portion 402 at one or more locations along a junction 412 between the belt portion 402 and the radiation shield portion 408. In some embodiments, such a proximity sensor system may be mounted in the radiation shield portion 408, for example, and may include one or more engagement sensors 416 disposed along or near the junction 412 and configured to detect that the shield portion 408 abuts the belt portion 402 in order to prevent or minimize radiation leakage, as shown in FIGS. 2 and 3A-3C. Many different types of sensors could be employed for engagement sensors 416, for example, including pressure sensors, Hall effect sensors, and magnetic sensors (e.g., where a ferromagnetic material is embedded into a vertical aspect of the belt portion 402, and the sensor is in the radiation shield portion 408, for example). A potential advantage to the use of a ferromagnetic sensor in certain embodiments is that the ferric material in the belt portion 402 can also be used to provide a magnetic attachment between the shield portion 408 and the belt portion 402 (thereby potentially enhancing both the detection and the engagement functions in such embodiments). A magnetic sensor, for example, may be configured to sense the degree of engagement between the shield portion 408 and the belt portion 402 at the junction 412, and/or may be configured to enhance the engagement between the shield portion 408 and the belt portion 402 at the junction 412. The proximity or engagement sensor system may, for example, optionally include an output, such as a visual indication which can be displayed to a worker using known methods of indicating fault/no fault, such as lights (for example, green for attached, and red for not attached), an electronic display (such as an LED tablet), or a mechanical display (e.g., where the sensor may be configured to mechanically alter an indicator flag upon contact with the belt portion 402).

An x-Ray Detection System to Ensure Adequate Radiation Shielding

An x-ray detection device or radiation sensing device may be housed in or coupled to the radiation shield portion 408 in a manner and/or location such that it is sensitive to the presence of radiation on the user side of the radiation shield portion 408. In one embodiment, for example, a radiation detector or sensor may comprise a thermo-luminescent detector ("TLD"), which may provide the advantage of fairly real-time detection of radiation levels. It is recognized that other types of radiation detectors and/or sensors can be used and that other detector types may be developed in the future. A radiation detector/sensor having a reasonably fast (e.g., real-time) output or indication of radiation (and additionally, radiation in excess of predetermined levels), such detectors/sensors could be suitable for use as a radiation detection alert system that may be utilized in conjunction with a shielding system in accordance with various embodiments disclosed herein.

A radiation detection device or sensor may be disposed near the worker, including for example, coupled or attached to the patient table or to any surrounding shielding devices that may be in use, such as the EggNest™ radiation protection system (from Egg Medical, Inc.), or to shields that hang from the ceiling, shields attached to the patient table, or shields that are placed on the floor near the patient table, as possible examples. In addition, detectors embedded in or reversibly attached to shields in the procedure room may allow for the detection and indication/display of radiation levels in the room. Rapid (e.g., real-time) detection of such radiation levels, and preferably also the locations thereof, may be useful for alerting personnel not to enter or stand in certain areas, or to move or re-position the shielding in the room to better block the radiation. Radiation detection sensors placed on or proximate to portions of the shielding system may be useful for assessing the positioning of the shielding system and/or its components, as well as for assessing the effectiveness of specific shields, for example.

An indication or display of the radiation level detected by the radiation detection device or sensor at the point of detection (e.g., at or near a portion of the shielding system) may be provided by lights or light emitters. In some embodiments, the color and/or intensity of the light emitted may be related to, or generally proportional to, the radiation level or intensity detected. In some embodiments, the intensity or level of the detected radiation may be indicated by flashing of the light, for example, flashing continuously, or flashing in a certain pattern or patterns, which could be used to represent or indicate the radiation intensity level. Similarly, sound could be used to indicate the intensity of radiation detected at the detector/sensor in some embodiments. For example, the tone, intensity, or pattern of sound could be used to indicate different levels of detected radiation. Vibration may also be used to indicate the intensity of radiation at the detector. The frequency or pattern or strength of vibration could be used to indicate different levels of detected radiation, for example.

In one embodiment, the x-ray sensor is configured to communicate with an x-ray system, such that the x-ray generation by the x-ray system, and the corresponding x-ray radiation levels thereby produced, may be inhibited and/or terminated upon sensing of an unsafe radiation level at a sensor/detector, and/or communication to the x-ray generation system that a certain predefined level of x-ray radiation intensity has been detected at one or more such sensors. Such a feature might prevent a user from receiving exposure to unsafe levels of radiation, or protect a user from unsafe exposure to radiation if the level of radiation detected exceeds a certain level, for example. The communication between the radiation detection sensors and the x-ray system could occur via communication methods as are known in the art, such as by wire, radio waves, light, or other communication methods, and the communication signal could be digital and/or analog in nature. The signal communicated from the sensor could, for example, consist of a simple on/off signal, or it could be an indication of the radiation intensity according to some embodiments. The x-ray generation unit or control system of the x-ray generation system may be controlled through an interface with one or more control systems of the x-ray system, including but not limited to interruption or modification of the current flow to the x-ray generator or the x-ray tube, through the software control system, or by interrupting or modifying the signal from a user-activated x-ray control switch (such as a floor pedal or a hand switch) according to certain embodiments.

Various embodiments of an innovative radiation shielding support structure are described in this disclosure. In some embodiments, a multi-articulated transparent shielding system is described that allows a user to bend a shielding structure comprising two or more clear shielding elements into a multitude of shapes without degrading the level of radiation shielding. The shield system may comprise one or more of the following:

A Flexible Radiation Shield System

With reference to FIGS. 6A-6C, a flexible or articulatable radiation shielding system 100 may comprise two or more shielding elements (e.g., shielding panes 10 and/or shielding frames 12) hingedly and/or pivotably coupled together to form an array of radiation shielding. For example, the articulatable radiation shielding system 100 may comprise a first shielding pane 10 and a second shielding pane 10. The shielding panes 10 may be formed of a clear (e.g., transparent or translucent) radiation blocking material, such as leaded glass or acrylic, for example. Exemplary shielding panes 10 are shown in FIG. 6A having a shielding frame 12 disposed or formed at least partially around an outer edge or periphery of each shielding pane 10. However, the shielding panes 10 may be arranged with or without a shielding frame 12 around the shielding panes 10 according to some embodiments. The shielding panes 10 may each have a top portion and at least one generally vertically oriented edge portion. A hinged coupling 14 may be provided between adjacent shielding elements (e.g., between adjacent pairs of shielding panes 10). For example, a hinged coupling 14 may pivotably couple a first shielding pane 10 to an adjacent second shielding pane 10 along the generally vertically oriented edge portions of each of the first and second shielding panes 10.

FIGS. 6A-6C also show several optional features that may be incorporated into a flexible radiation shield system 100 according to this disclosure. For example, a cable 24 may be included along a top portion of an array of shielding elements (e.g., along a top portion of shielding panes 10 and/or shielding frames 12) to limit the amount of bending of the flexible radiation shield system 100. Cable 24 may be disposed along a top portion of each shielding pane 10, for example, to function as a hinge connector to couple the shielding panes 10 to one or more hinged couplings 14. FIG. 6A shows optional handles 22 that may be included at one or both ends of radiation shield system 100 to facilitate placement. FIG. 6A also indicates a potential conforming contour or cutout shape 26 that may be employed in a radiation shield system 100 in order to accommodate the shape and/or size of a typical patient (not shown). For example, the area below the dashed line indicating the cutout shape 26 would be removed (e.g., the affected shielding panes 10 and/or shielding frames 12 would be shaped and formed accordingly) to form the desired cutout shape 26 to conform to the contour of a patient, for example. FIG. 6B shows an attachable cap 28, which may be used in some embodiments of this disclosure in order to couple or connect the various other elements of a radiation shield system 100, for example, hinged coupling 14 (e.g., inner rod 20 and/or outer tube 18, to be described below), adjacent shielding panels and/or frames 10, 12, cable 24, hinge shield 16 (to be described below), etc.

Detailed views of the hinged connection or hinged coupling 14 are shown in greater detail in FIGS. 6B and 6C. FIG. 6B, for example, is an enlarged front view of a portion of a flexible radiation shielding system 100 according to some embodiments, showing a hinged coupling 14 comprising on outer tube 18 and an inner rod 20 disposed within the outer tube 18, arranged to provide a hinged coupling between adjacent shielding elements (e.g., shielding panes 10 and/or shielding frames 12). The outer tube 18 and inner rod 20 may be formed of suitable materials, such as various metals, for example. The outer tube 18 and/or inner rod 20 may have some inherent radiation shielding properties or may optionally be formed of materials having additional radiation shielding properties, but this is not necessarily required. The outer tubes 18 may be free-floating in some embodiments, or may be attached to one or more shielding panes 10 or shielding frames 12 in certain other embodiments. The outer tube 18 functions to cover the inner rod 20 at the hinged coupling 14 between adjacent shielding panes 10. In some embodiments, the outer tube 18 may offer some level of shielding and/or may offer a structure upon which additional shielding may be placed. In an alternate embodiment, the outer tube 18 may be provided without the inner rod 20, for example by having hinged or rotatable couplings directly between a shielding element and the outer tube 18. In some embodiments, a radiation blocking plate (e.g., hinge shield 16) may be additionally provided to cover gaps around edges of shielding elements (e.g., around shielding panes 10 and/or shielding frames 12), for example. FIG. 6C is an enlarged top plan view of a portion of an exemplary flexible radiation shielding system 100, showing the exemplary hinged coupling 14 of FIG. 6B. As shown in FIG. 6C, a radiation blocking plate or shield such as hinge shield 16 is disposed proximate the hinged coupling 14 in order to provide radiation shielding protection at or along the interface between adjacent shielding panes 10 and/or shielding frames 12. Hinge shield 16 is an exemplary mechanism or means for blocking radiation between adjacent shielding panes 10 when these elements are articulated (e.g., pivoted, rotated, angled, etc.) relative to one another, for example, in order to cause the radiation shield system 100 to assume a convex shape, or a concave shape, or a combination of convex and concave shapes along portions thereof (Examples of such articulatable shapes that may be formed by a radiation shield system 100 are illustrated in FIGS. 7A-7C.) The hinge shield 16 may, for example, be comprised of a number of radiation blocking materials, such as lead, polymers loaded or embedded with radiation blocking materials, etc. The hinge shield 16 may be formed of opaque or transparent shielding materials according to various embodiments.

In some particular embodiments, the outer tube 18 and inner rod 20 are both components of a hinge mechanism (e.g., hinge coupling 14). For example, the outer tube 18 may be connected or coupled to a first shielding pane 10 or shielding frame 12 on one side, and the inner rod 20 may be connected or coupled to a second shielding pane 10 or shielding frame 12 disposed on the opposite side of outer tube 18. This may allow two shielding elements (e.g., panes 10 and/or frames 12) to be joined (e.g., along an adjacent vertical edge), while also being able to rotate or pivot relative to one another. The hinges 14 may either be manufactured from material that provides sufficient radiation-blocking properties or may have shielding materials arrayed about it such that scatter radiation cannot pass through gaps between the shielding panes 10 of the shield system 100.

In some embodiments, the hinge shield 16 may provide radiation-blocking protection equivalent to that of 0.5 mm thickness of lead or more. In some embodiments of this disclosure, it is preferred that the shielding panes 10 provide radiation-blocking protection equivalent to that of 1.0 mm thickness of lead or more. The shielding panes 10 may be provided in shapes other than strips or rectangles, for example. Moreover, the shielding properties of a given shielding pane 10 may differ from other shielding panes 10, and/or may be adjusted for the anticipated radiation exposure at a particular shielding pane 10 based on the position of the shielding pane 10 relative to other shielding panes. For example, the shielding panes 10 disposed at an end (e.g., an outer portion) of the hanging shield (e.g., radiation shield portion 408) may have 0.5 mm lead equivalence radiation shielding protection, whereas a more centrally disposed panel or panels of shield portion 408 may be configured to have a higher level of radiation shielding protection (e.g., a 1.0 mm lead equivalency or greater, for example) because it is anticipated that the centrally disposed shielding panes 10 will be exposed to higher levels of radiation.

Figure 6D:
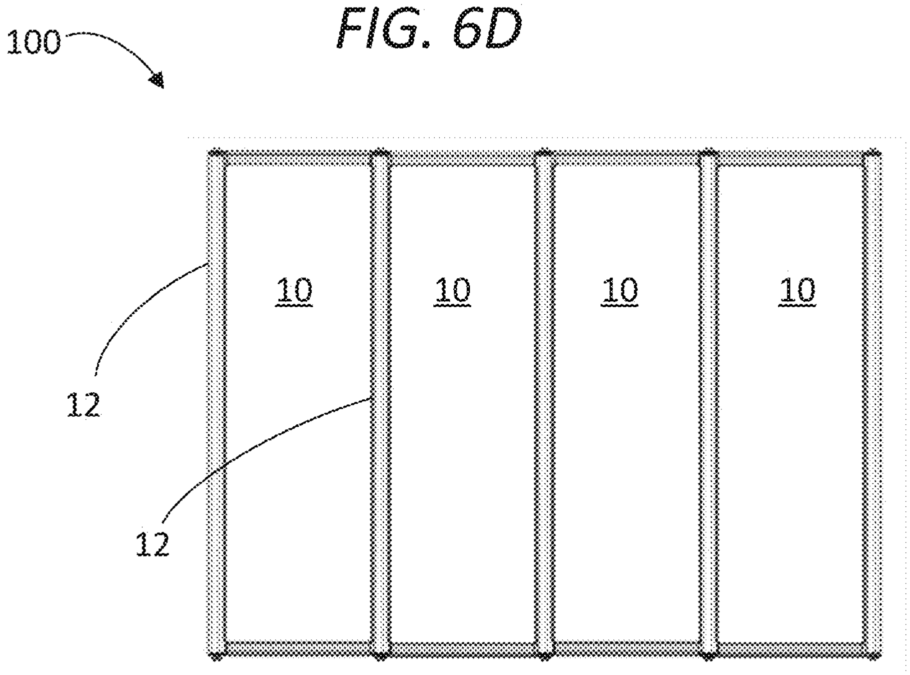
FIG. 6D is a front view of a flexible radiation shielding system according to some embodiments of this disclosure.
Figure 6E:
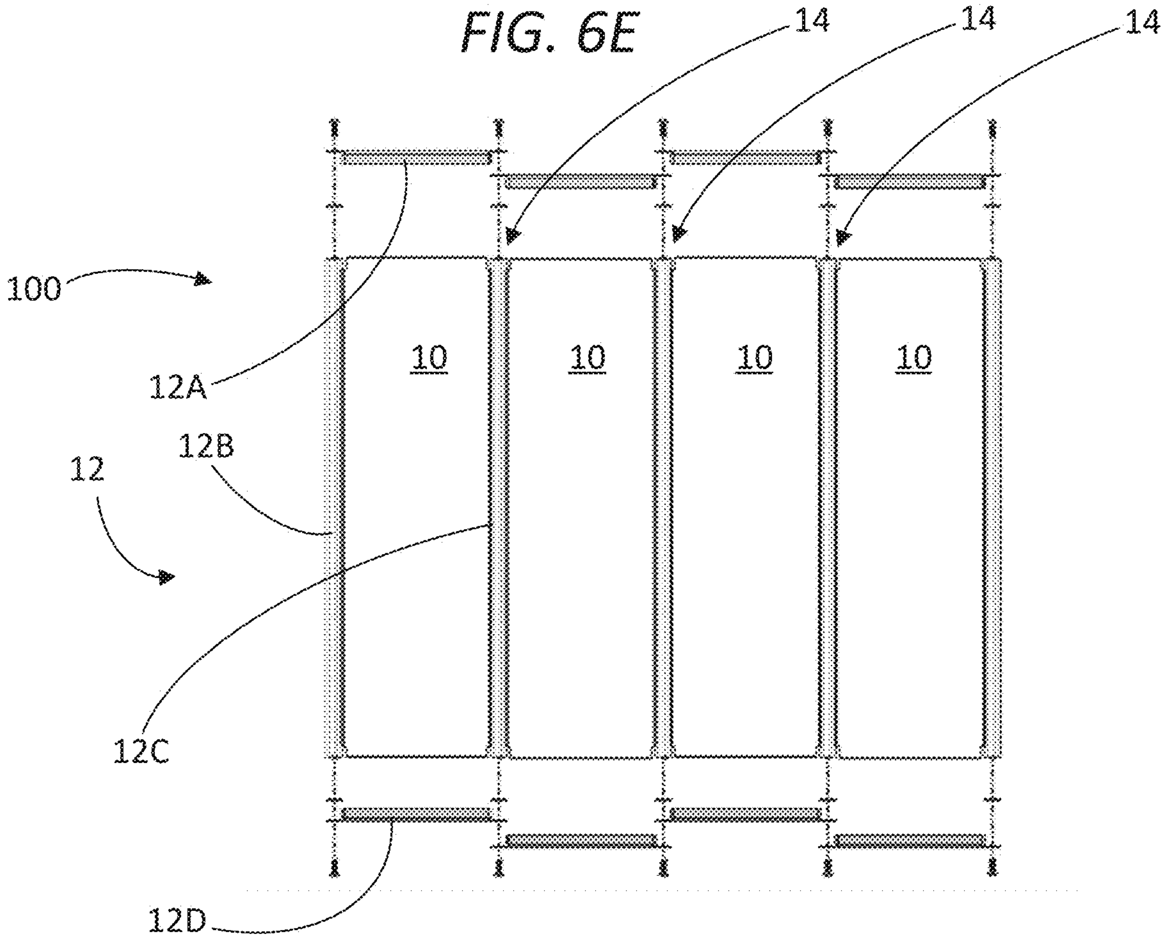
FIG. 6E is an exploded front view of a flexible radiation shielding system according to some embodiments of this disclosure.
Figure 6F:
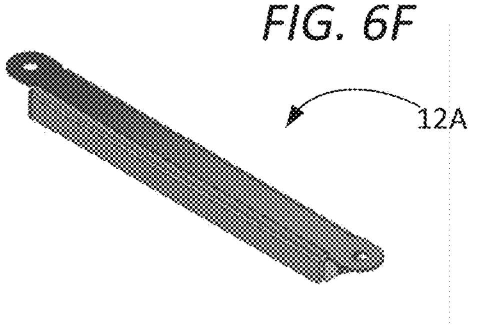
FIGS. 6F-6I are perspective views of various elements of the flexible radiation shielding system of FIG. 6E according to some embodiments of this disclosure.
Figure 6H:
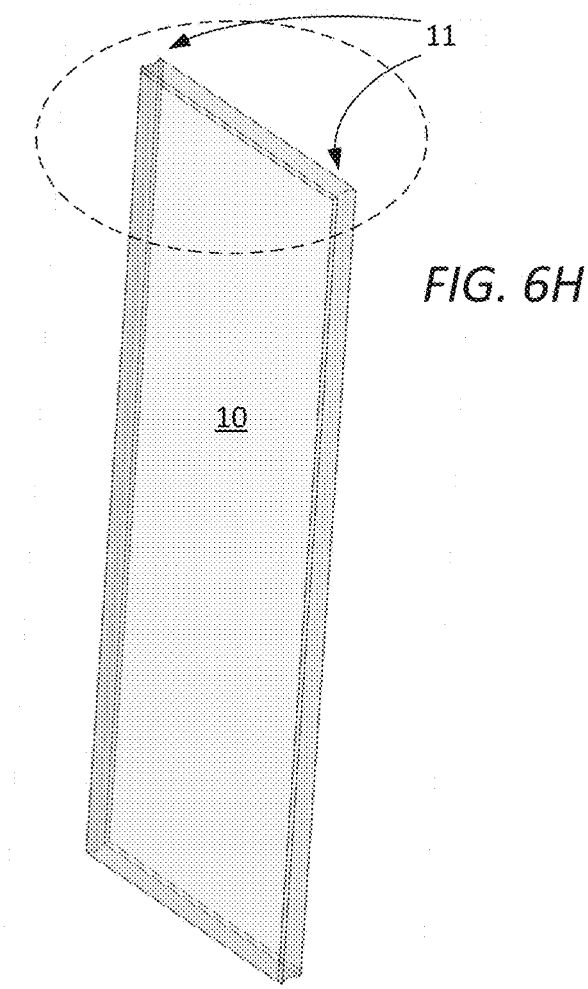
Figure 6G:
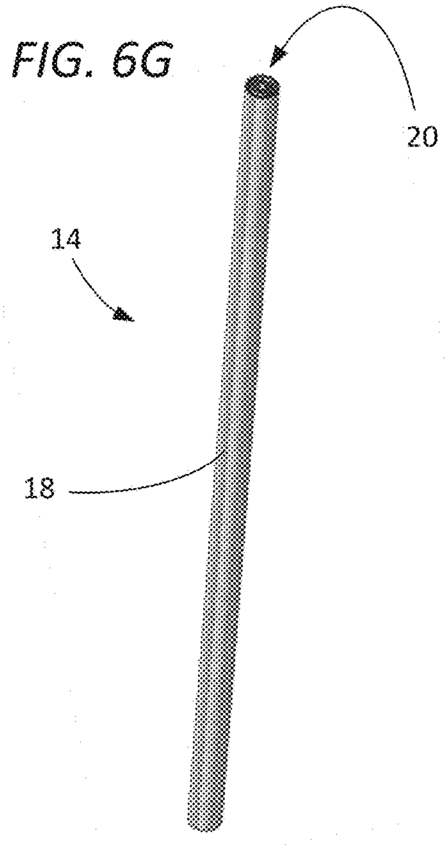
Figure 6I:
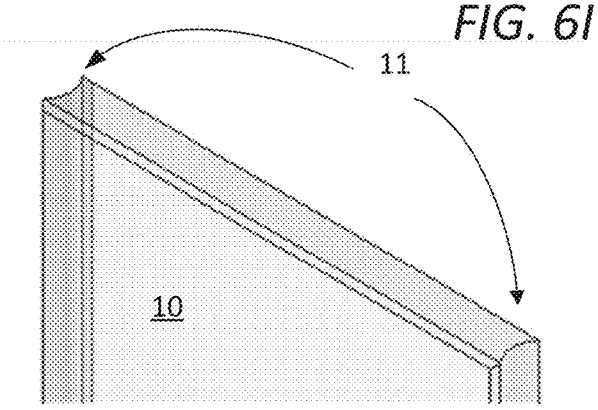
Figure 7A:
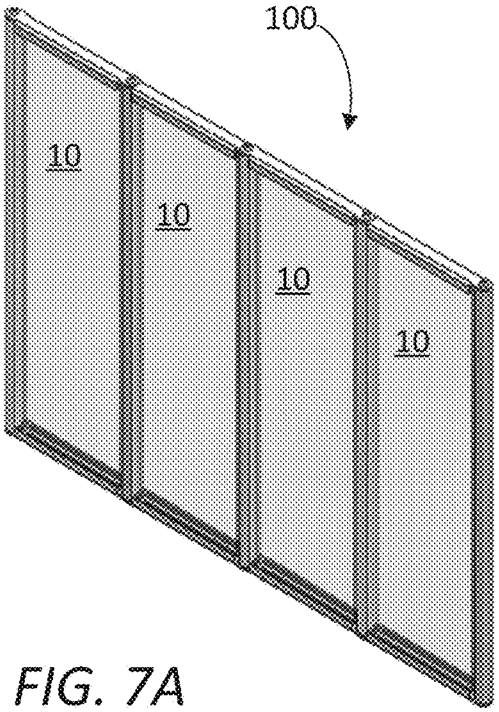
FIGS. 7A-7C are perspective views of a flexible radiation shielding system configured in various exemplary shapes enabled by some embodiments of this disclosure.
Figure 7B:
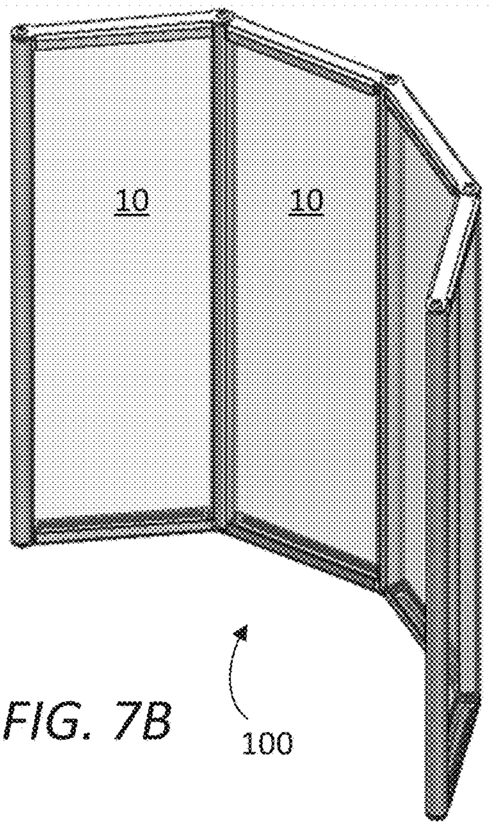
Figure 7C:
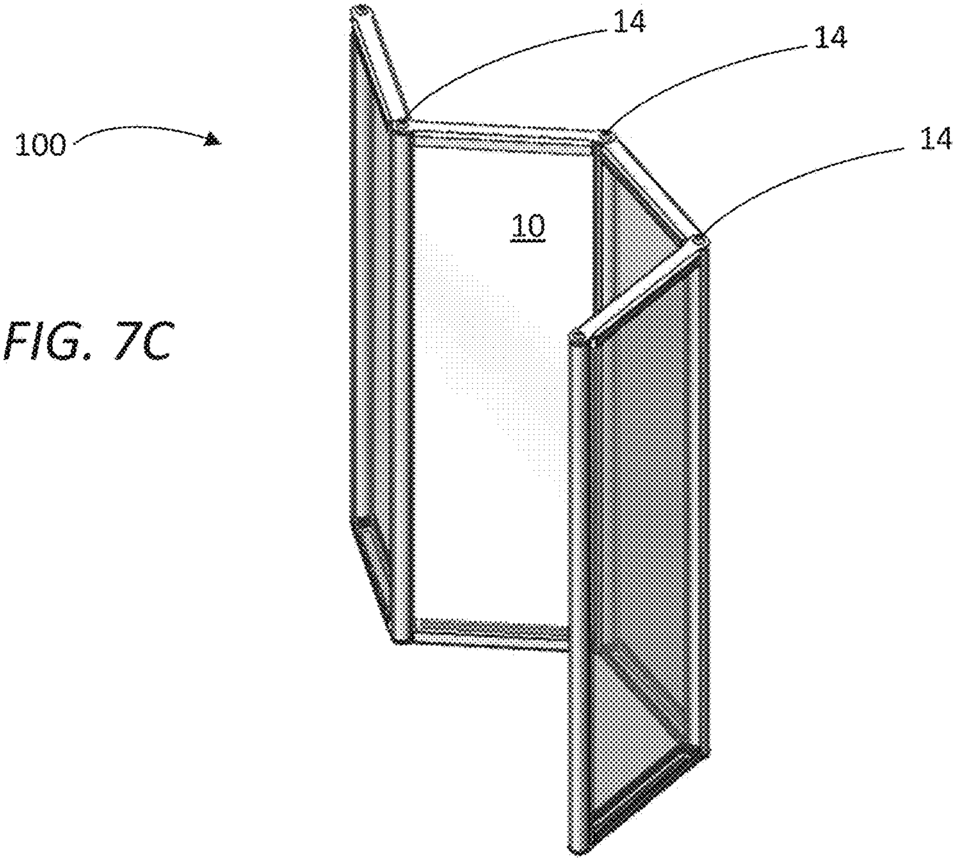

FIGS. 6D-6I show details of a particular embodiment of a flexible radiation shield system 100 according to some embodiments of this disclosure. FIG. 6D is a front view of exemplary radiation shield system 100 comprising a four-panel array of shielding elements formed of shielding panels 10 and shielding frames 12. FIG. 6E is an exploded front view of the exemplary radiation shield system 100 of FIG. 6D, showing an arrangement of elements forming shielding frame 12 in a manner that may enable relative pivoting or angling of adjacent shielding panes 10, for example. FIG. 6F shows a single top portion of shielding frame 12, with end portions having receptacles configured to facilitate coupling to an outer tube 18 and/or inner rod 20 of hinged coupling 14, for example. FIG. 6G shows outer tube 18 and inner rod 20 (e.g., disposed within outer tube 18) of hinged coupling 14. It should be noted that, in some embodiments, a single pole or tube 18 (e.g., solid or hollow) could be used to facilitate pivotable or hinged coupling. Outer tube 18 and/or inner rod 20 may also be used to block radiation (e.g., if formed of suitable radiation blocking materials), or could be lined or coated to perform that function, according to some embodiments of this disclosure. FIG. 6H shows a shielding pane 10 according to certain embodiments of this disclosure, where a concave shape 11 is formed in one or more generally vertically oriented edge portions of the shielding pane 10. FIG. 6I is an enlarged view of the dotted line inset of FIG. 6H, showing details of the concave shape 11 formed in shielding pane 10. The concave shape 11, may enable an outer tube 18 disposed therein (or adjacent thereto) to form a relatively close, overlapping engagement with the edge of shielding pane 10. This may, for example, enhance radiation blocking between adjacent shielding panes 10, while continuing to allow for pivotable adjustment between adjacent shielding panes 10. As noted above, flexible adjustment of the angle (e.g., in some cases, forming an angle or arc of up to about 30 degrees or more from a straight array) between adjacent shielding panes 10 and/or frames 12 may enable the formation of numerous overall shapes for the flexible radiation shield system 100 (see FIGS. 7A-7C, for example). For example, the exemplary radiation shield system 100 of FIGS. 7A-7C comprises a four-panel array of shielding elements formed of shielding panels 10 and shielding frames 12. Radiation shield system 100 could similarly comprise an array of two or three shielding elements, or an array of five or more shielding elements according to various embodiments. Flexible adjustment of the angle between adjacent shielding panes 10 and/or frames 12 of radiation shield system 100 may enable the shaping of radiation shield system 100 into a range of convex or concave shapes (e.g., as seen from above), such as the shape/configuration shown in FIG. 7B, or into an "S"-shaped configuration, such as that shown in FIG. 7C, as just two exemplary possibilities.

FIG. 8A is a front view of a flexible radiation shielding system 200 according to some alternate embodiments of this disclosure. Flexible radiation shielding system 200 comprises two or more radiation blocking elements (e.g., shielding elements or shielding panes 10), wherein some or all of the shielding elements consist of a substantially clear surface with a shielding hinge joint 214 that is integral to the shielding pane 10, such that multiple shieling elements 10 can be assembled together to form a flexible shield 200, as shown in FIG. 8A.

FIGS. 8B and 8C are enlarged top views of a shielding hinge joint 214 arrangement for a flexible radiation shielding system 200 according to some embodiments of this disclosure. As shown in FIGS. 8B and 8C, a plurality of shielding panes 10 may be releasably coupled together and/or disconnected as needed (e.g., via a friction fit, using a ball and socket configuration or similar, as shown) to vary the overall size, shape, and protective coverage of the resulting shielding system 200. FIG. 8D shows an embodiment in which a shielding element 210 comprises a shielding pane 10 having shielding hinge joints 214 formed along opposite sides or ends (e.g., a "male" hinge joint 214 at one end and a "female" hinge joint 214 at the other end, comprising the ball and socket configuration described above) and along opposite lengths of shielding element 210. In this embodiment, the individual shielding elements 210 and hinge joints 214 are formed of a one-piece shielding material. This enables the "socket" hinge joint 214 formed along one edge of a shielding element 210 to releasably couple or mate with the "ball" hinge joint 214 of another shielding element 210, and thereby allows two adjacent shielding elements 210 to be pivoted or rotated relative to each other along an axis formed by a length of the respective hinge joint 214, for example.

In addition, the following features and/or components may be added to the radiation shielding systems 100 and/or 200 described above, according to various alternate embodiments of this disclosure to add functionality and/or flexibility to systems 100 and/or 200, as described below:

In some embodiments, a hinged coupling 14 (e.g., outer tube/inner rod 18, 20 arrangement) or a hinge joint 214 (e.g., a ball and socket arrangement) may enable a pivotable or rotatable connection between shielding elements to be reversibly locked at a desired angle, for example. A reversible locking mechanism may enable an array of shielding elements to be shaped or formed as desired, and then reversibly locked or fixed into the desired shape (including locking or fixing one or more of the angles between shielding elements with respect to each other). After use, the reversible locking mechanisms could be released to enable storage of the shielding system 100, 200 (e.g., to enable straightening the array of shielding elements, or folding into a flat configuration, or separating one or more shielding elements from the overall system, etc.), or to enable shaping of the shielding system 100, 200 for a subsequent different usage, etc. The individual shielding elements could be separated or joined as needed to vary the overall dimensions of the array of shielding elements. This feature allows the user to set a specific configuration or shape for the shielding system 100, 200, and then lock it into place, with the ability to unlock and reconfigure the shape, etc.

A reversible locking mechanism may take a number of forms. A simple ball-detent lock could, for example, snap into place while allowing the shielding panes 10 to be "unsnapped" with a simple force applied to the assembly. A friction lock is another option that could be used that relies on the relative force required to shape the array of shielding elements (e.g., to change the angle between adjacent shielding panes 10 by overcoming frictional resistance) being higher than the force to move the shielding system 100, 200 around. Such a friction hinge would be able to maintain the overall shape of the array of shielding elements until it is desired to change. The reversible locking mechanism may, for example, comprise a spring-loaded button that toggles so that, when pushed initially, it locks the hinge or ball/socket into a fixed or locked position, and that when pressed again, would release the locking mechanism to enable pivotable movement of the shielding panes 10 relative to each other; the reversible locking mechanism could, for example, maintain the physical coupling between adjacent shielding panes 10, while only affecting the ability to rotate or pivot with respect to each other. The exemplary button to actuate the reversible locking mechanism could either push into a hole on an internal feature inside the hinge construction, or could increase friction internally by compressing a sleeve in the hinge assembly preventing movement. This effect could also be accomplished in ether configuration by using a lever or similar mechanical actuation device, rather than a button.

When the shielding elements include shielding frames 12 (e.g., in addition to shielding panes 10), the shielding frames 12 may be provided with an open or openable end of the frame 12 such that the shielding element (shielding pane 10) can be removed and/or replaced. An example of this configuration is shown in the exploded view of FIG. 6E, where shielding frames 12 are formed of multiple frame elements, such as "top" frame element 12A (see FIG. 6F, for example), which is removably coupled to the other frame elements (e.g., frame elements 12B, 12C, and 12D of FIG. 6E, for example) of shielding frame 12 with any of a variety of fasteners (e.g., bolts, nuts, threaded mechanisms, etc.). Frame element 12A, in such embodiments, becomes a removable portion of the associated shielding frame 12. Removal of a top frame element 12A could thereby create an openable end of shielding frame 12 enabling removal and/or replacement of shielding pane 10. Of course, in some embodiments, it may be preferable to remove a different frame element, such as "bottom" frame element 12D of FIG. 6E. Other methods of replacing and/or removing shielding panes 10 would be apparent to those of ordinary skill with the benefit of these teachings. In some embodiments, top frame element 12A, disposed along a top portion of a shielding pane, may function as a hinge connector configured to couple an associated shielding pane 10 to a hinged coupling 14.

Shielding elements (e.g., shielding panes 10) may comprise multiple layers in some embodiments. As but one such example, a shielding element may include a layer formed of a leaded glass element sandwiched between two layers comprised of polymer elements, for example, to thereby contain any loose glass fragments that might become present due to a fracture of the leaded glass portion of the shielding element. The various layers of the shielding element may be clear, transparent, or translucent, according to various embodiments.

In some embodiments, the shielding elements (e.g., shielding panes 10) may comprise adjustable elements such that the length and/or width of the shielding element could be varied/changed by slidably moving (e.g., translating) one such adjustable element relative to the other, along a track or other sliding mechanism. This could be done, for example, by using multi-layer shielding elements configured to move relative to each other (e.g., adjacent surfaces sliding past each other).

In some embodiments, a continuous resistive element may be coupled to the radiation shielding system 100, 200. Such a resistive element may limit the bending of one or more hinged couplings 14 or hinge joints 214 when force is applied to the lateral aspects of the shielding system 100, 200 in order to bend the overall shape of the shielding system 100, 200 into a concave or convex shape, for example. The resistive element may act to coordinate and/or limit the bending or shaping of the shield system at the various hinged couplings 14 or hinge joints 214 in response to a force applied to the shielding system. The resistive element may be composed of one or more elements of the same or a different resistive capacity. An example of a simple resistive element that may provide desired degree of stiffness is a soft aluminum wire, such as cable 24 shown in FIGS. 6A-6C. A multi-articulated resistive element, such as an articulated hose, may also be used, and the resistance between the articulations may be adjusted to modulate the degree of bending at each hinged coupling 14 or hinge joint 214 when the shield system 100, 200 is subject to a bending or shaping force.

In some embodiments, a flexible, non-transparent shielding may be attached to the edges of the shielding element or shielding elements to better conform to the shielded object (such as a patient's body, for example).

A Mechanism of Support

A support structure for a radiation shielding system is described according to certain embodiments of this disclosure. The support structure can take many configurations, depending on the desired functionality and the environment into which it is placed.

In one configuration, shielding system 100, 200 may be attached to a boom. The boom, in turn, may be mounted to the room ceiling (e.g., suspended from a support coupled to the ceiling of the procedure room) or to a suspension device (e.g., a floor-mounted device with support arms). The attachment may be made from the end of the boom arm to a shielding element. For example, the attachment may be from a distal end of the boom to a shielding pane 10 or a shielding frame 12 disposed near the center of the shielding system 100, 200, for example. The attachment from the boom to the ceiling or suspension device may have anywhere from zero to three degrees of freedom, according to various embodiments. Similarly, the attachment from the boom to one or more shielding panes 10 and/or shielding frames 12 of the shielding element array may also have from zero to three degrees of freedom, depending on the desired use.

In another configuration, the suspension mechanism may be coupled to two or more portions of the shielding system 100, 200, for example, it may attach to two or more shielding panes 10. Such a configuration (e.g., having more than one coupling points or attachment points) may provide a benefit, such as more stability to the shielding system 100, 200. The tilt of the attachment mechanism can be fixed or variable though the use of extendable members, such as a telescoping rod.

In another configuration, the radiation shielding system 100, 200 may be supported by the floor of the procedure room, such that it is supported by wheels or feet that rest on the floor.

In another configuration, the suspending mechanism attachment can be reversibly locked to provide stability, for example. Reversible locking could occur at a proximal end of the boom of the suspension mechanism, or a distal end of the boom of the suspension mechanism, or possibly at both ends.

The radiation shielding system 100, 200 may also be configured to be reversibly or removably attached to the procedure table 502, or to a rail system attached to or integral with the procedure table 502 or pedestal, or a structure coupled to the procedure table 502, or by an adhesive attachment to the patient 500 and/or the patient sterile draping material. The attachment may be configured such that it has zero to three degrees of freedom to thereby accommodate procedure table 502 movement, as well as movement of the radiation shielding system 100, 200 in concert with movement of the procedure table 502. In such a configuration, the radiation shielding system 100, 200 may be supported by a suspending member rather than by the procedure table 502.

Shielding Array Support System

Another aspect of an innovative shielding structure according to embodiments of this disclosure is a shielding array support system that may be used to configure radiation shielding (e.g., x-ray shielding) around a procedure table where and as needed, adapting the shielding (for example, to the type of procedure being performed) in order to provide radiation protection for a primary operator and others working in the lab or procedure room.

One component of such a shielding array support system is a base structure that allows for the attachment of shielding components and other accessories around a lab/procedure table without the use of certain components (e.g., radiopaque components) that might interfere with or otherwise affect x-ray imaging procedures. This base structure may be designed to enable one or more other components to attach to, couple to, or mate with the base structure to facilitate mounting of shielding and other accessories on an as-needed and/or where-needed basis.

Figure 9A:
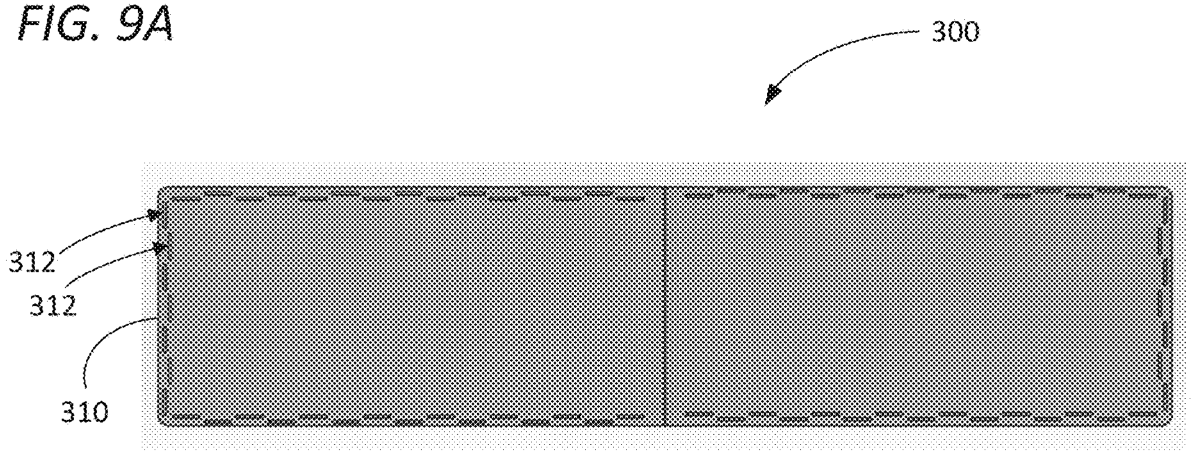
FIGS. 9A and 9B are top plan views of a base unit for a shielding array support system according to some embodiments of this disclosure.

FIG. 9A is a top plan view of a base unit 310 for a shielding array support system 300 according to some embodiments of this disclosure. The base unit 310 may be manufactured from a number of suitable radiolucent materials, such as carbon fiber, polymer, or other similar materials. Such radiolucent materials may be used to form base unit 310 in order to limit or avoid imaging artifacts that might arise during use of shielding array support system 300, such as during radiographic imaging procedures. Base unit 310 may be a flat sheet or a three-dimensional machined, cast or molded component. Base unit 310 may be formed to support a patient and/or a patient mattress disposed thereon.

Base unit 310 may include one or more slots or holes 312 positioned near a periphery of base unit 310. A plurality of slots/holes 312 positioned near the periphery of base unit 310 may extend through the thickness of base unit 310 in some embodiments, or may extend partially through base unit 310 in other embodiments. In some embodiments, a series or pattern of slots or holes 312 may be positioned around or adjacent to an outer perimeter or periphery of base unit 310. In some embodiments, the holes or slots 312 may form multiple rows (e.g., two rows shown in FIGS. 9A and 9B) around the periphery of base unit 310. In some embodiments, the slots or holes 312 in adjacent rows may be offset from each other, etc., to enable or facilitate some degree of flexibility in positioning and/or placement of accessory items thereon, for example. In some embodiments, slots or holes 312 may act as sites of attachment for accessory shielding components, shielding support elements, armboards, workbenches, secondary rails, or other components for example. In various configurations, slots or holes 312 may range in length from about 1.5" to 3.5". It may be desirable for certain slots or holes 312 to vary in length. As but one exemplary embodiment, an outer row of slots/holes 312 may be about 2.5" in length, with an inner row of slots/holes 312 being about 1.5" in length. The longer slots (e.g., in this example, the holes/slots 312 of the outer row) may allow for the placement of tabs (e.g., tabs extending from an attachable/detachable accessory or component) that are more capable of carrying heavier loads; bigger/longer slots/holes 312 may therefore be selected in areas in which the attached components are expected to be load-bearing. An inner row of slots/holes 312 may, for example, be used to maintain spatial orientation for certain non-load-bearing and/or lightweight components. The use of slots/holes 312 of varying lengths may also facilitate avoiding confusion among users regarding where to place certain components when system assembly is performed. The slotting pattern may be selected to facilitate placement of components anywhere around the shielding array support system 300 desired by an operator. This may, for example, allow for a procedure to be performed either with or without the use of one or more shielding support elements, such as armboards or "wings" 320 removably mounted to the base unit 310, or with shielding either attached to a shielding support element (e.g., wing 320) or moved inward to the edge of the base unit 310 when the wing 320 is removed, etc. A level of flexibility and/or customization may be thereby realized to facilitate or optimize placement of shielding for any procedure performed with the shielding array support system 300.

Figure 9B:
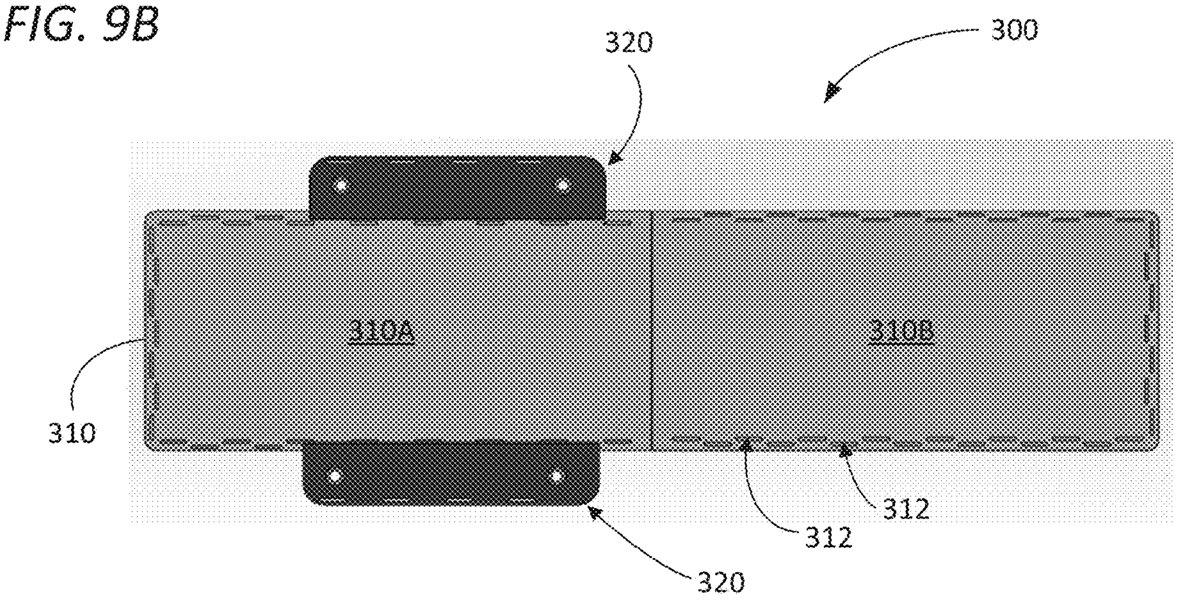

FIG. 9B is a top plan view of a base unit 310 having one or more wings 320 placed thereon for a shielding array support system 300 according to some embodiments of this disclosure. Each shielding support element (such as wing 320) may be removably mounted in holes/slots 312 of base unit 310 via one or more tabs or tab portions (not shown in FIG. 3B) extending downwardly from an edge portion of wing 320, for example, and being sized and shaped to fit within slots/holes 312. The wings 320 may have connection or mounting tabs that mate with certain slots/holes 312 in the base unit 310. The pattern of tabs extending from wing 320 (e.g., the number, spacing, etc.) may allow wing 320 (or other similar structures, components, accessories) to be movably and/or removably mounted at many different points around the base unit 310. The tab portions of various shielding support elements are configured to be selectively positioned within one or more of the plurality of slots/holes 312 to removably mount the shielding support elements. In turn, certain shielding support elements may also be formed having a plurality of slots/holes positioned near a periphery of the respective shielding support elements, according to some embodiments. This may allow for relatively simple changes to be made to the shielding configuration of the procedure table, for example, to adapt to various procedure types and corresponding radiation protection needs. Removal of all components (including, for example, wings 320) from base unit 310 may allow for full imaging of a patient, including 360-degree x-ray spins around the patient without interfering with the range of motion of the x-ray system and/or without compromising image quality. The depth of slots/holes 312, and the corresponding length of the tabs extending from the wing 320 may enable the wing 320 to be supported with a substantially horizontal surface extending away from a side of base unit 310 when removably coupled thereon. In the example shown in FIG. 9B, there are two wings 320 removably coupled to one side or one half (e.g., upper half 310A) of base unit 310. As needs change, more (or fewer) wings 320 may be coupled to (or uncoupled from) base unit 310, including the upper half 310A or lower half 310B of base unit 310.

Figure 9C:
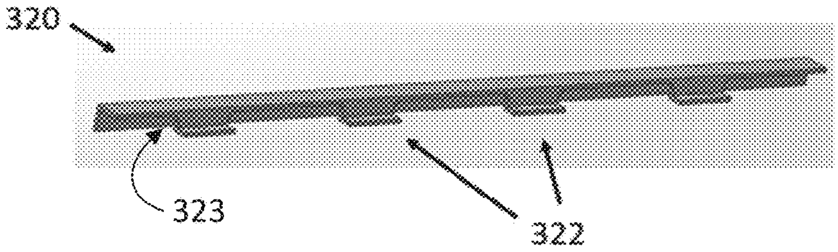
FIGS. 9C and 9D are perspective views of a wing or armboard having a number of tabs to facilitate removable mounting to a base unit of a shielding array support system according to some embodiments of this disclosure.
Figure 9D:
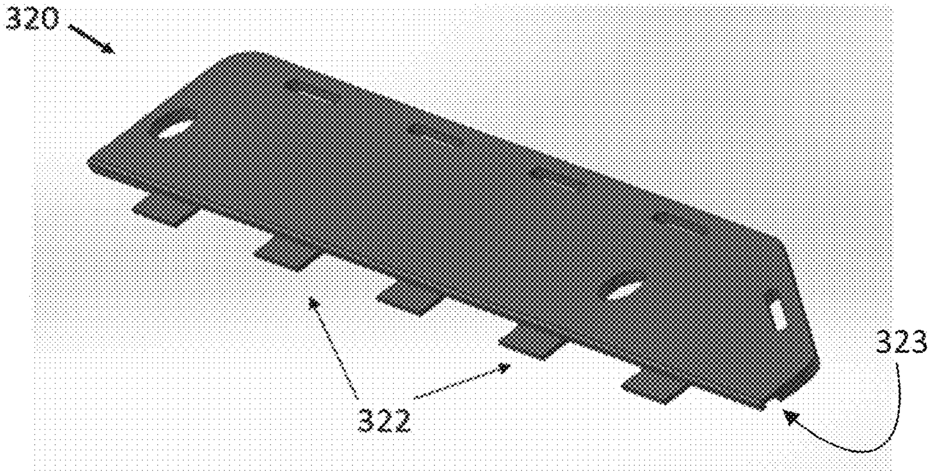

There are a number of tab arrangements that may be used to facilitate removably mounting and/or supporting armboards or wings 320 or other components via the plurality of slots/holes 312 positioned about the base unit 310. As one example, FIG. 9C is a rear perspective view of a wing 320 showing a "stepped tab" configuration. Tab portions 322 in FIG. 9C comprise one or more stepped tabs that may be selectively positioned and inserted into the slots/holes 312 in a substantially vertically-oriented manner, and wing 320 is then rotated in a downward and/or outward direction to engage tab portions 322 within slots/holes 312 of base unit 310, with the tab portions 322 seated in a substantially horizontal orientation. As shown, the stepped tab portions 322 may include substantially vertical and substantially horizontal portions to engage within the slots/holes 312 (e.g., an "L-shape" in some embodiments) and/or to an adjoining surface of the base unit 310. The stepped tab 322 design may be able to support a relatively large load on the surface of the component (e.g., wing 320), for example. FIG. 9D is a top rear perspective view of an armboard 320 showing a "stepped tab" 322 configuration similar to that described with respect to FIG. 9C.

Figure 9E:
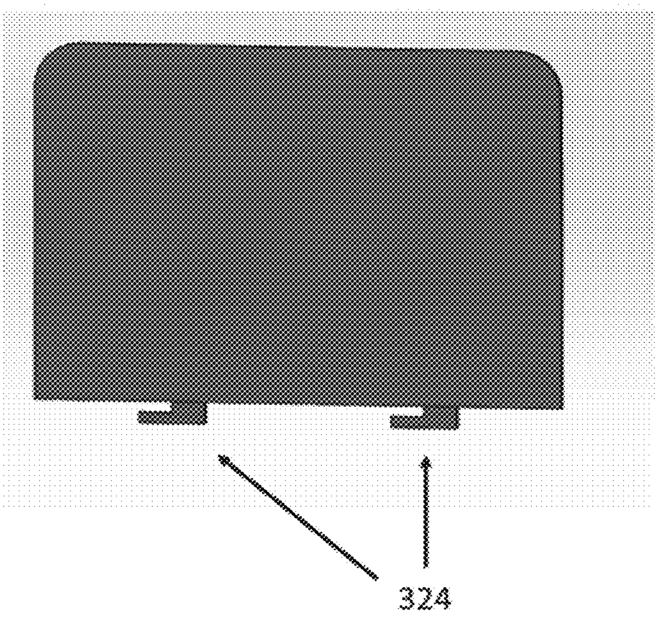
FIG. 9E is a side view of a shielding element or accessory component with undercut notched tabs for engaging with a base unit of a shielding array support system according to some embodiments of this disclosure.

FIG. 9E is a cross-sectional side view of another tab arrangement for an exemplary shielding support element comprising a vertical tab portion with an L-shaped undercut notch, as shown by tab portions 324. The tab portion 324 may be configured to extend downwardly into at least one of the plurality of slots/holes 312 and may extend under at least a portion of the base unit 310 (e.g., the tab portion 324 may extend either cranially, towards a head portion of the base unit 310, or caudally, towards a foot portion of the base unit 310). In using such an embodiment, each tab portion 324 may be lowered or extended downwardly into at least one of the plurality of slots/holes 312, and the associated shielding support element may be moved along the slot/hole 312 either cranially or caudally (e.g., toward the head or the feet of a patient, for example) to engage the notched tab portion 324 with the slots/holes 312 of the base unit 310. For example, a base unit 310 may include one or two (or even more) rows of slots/holes 312 as described previously with respect to FIG. 9A. The pattern of slots/holes 312 in one row may be offset (e.g., staggered) from slots/holes 312 of another row (e.g., in a configuration where the rows of slots/holes 312 comprise an inner row and an outer row) so that the tab portions 324 that are selectively positioned through a slot/hole 312 in one row do not interfere with the other row of slots/holes 312, maintaining or maximizing the functional use of all (or almost all) of the slots/holes 312 on the base unit 310. In other words, the position of at least one of the slots/holes 312 of the inner row may be staggered or offset along the periphery of the base unit 310 from an adjacent slot/hole of the outer row of slots/holes 312. This type of tab engagement design may be suited for placement of radiation shields and/or light-load bearing applications.

Figure 10A:
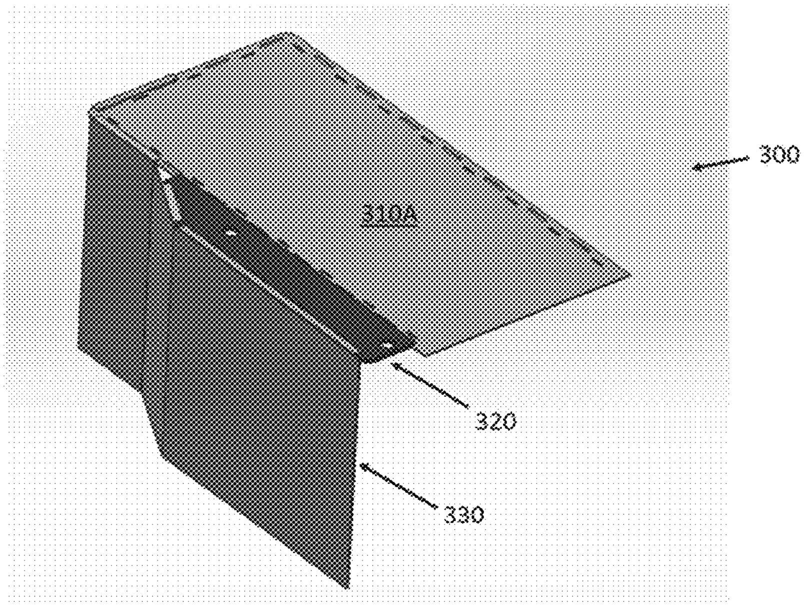
FIG. 10A is a top perspective view of a portion of a base unit, a wing or armboard, and shielding elements of a shielding array support system according to some embodiments of this disclosure.

FIG. 10A is a top perspective view of a portion of a base unit 310 (upper portion 310A), a wing 320, and shielding 330 extending downwardly from base unit 310 of a shielding array system 300 according to some embodiments of this disclosure. A shielding element, such as shielding 330, for example, may be configured to be removably mounted or attached to the base unit 310, for example, via channels that lock into slots/holes 312 on either or both of base unit 310 and/or wing 320 (as shown in FIG. 10A), or on other components mounted similarly to base unit 310. As noted above with respect to wings 320, shielding 330 and certain other ancillary components may have connection tabs 322, 324 that match with the plurality of slots/holes 312 in the base unit 310, the pattern of which may allow such components to be mounted at many points around the base unit 310 as requirements may dictate and change. This may allow for simple changes to the radiation shielding configuration of the procedure table to adapt for multiple types of procedures. Removal of components from the base unit 310 may allow for more complete imaging of the patient, including 360-degree x-ray spins around the patient without interfering with the range of motion of the x-ray system or with image quality.

Figure 10B:
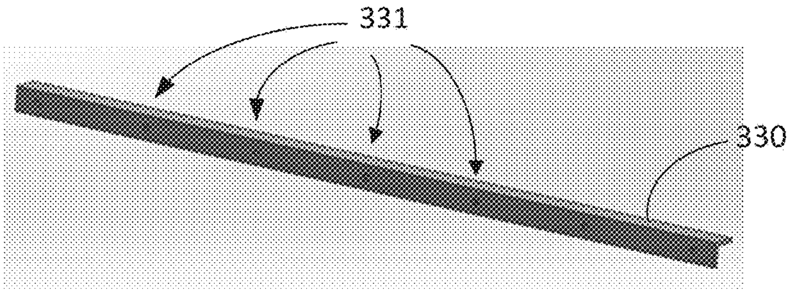
FIGS. 10B and 10C are perspective views of exemplary mechanisms for mounting shielding elements to an accessory component of a shielding array support system according to some embodiments of this disclosure.
Figure 10C:
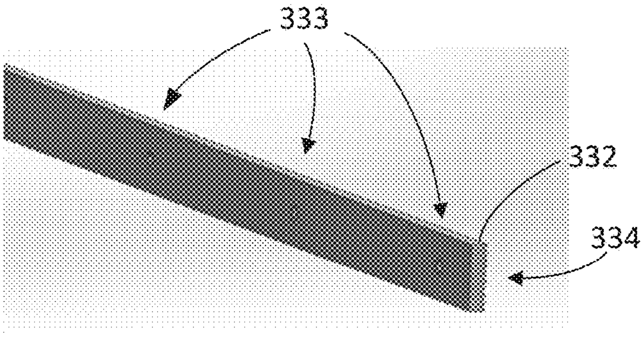

FIGS. 10B and 10C are front perspective views of exemplary mechanisms for mounting shielding to an accessory component of a shielding array system according to some embodiments of this disclosure. For example, shielding 330 may be coupled to the wings 320 via a tabbed u-shaped channel 323, for example, formed in an underside of wing 320 (see u-shaped channel 323 formed in wing 320 in FIGS. 9C and 9D). The shielding 330 may, for example, be provided with a series of holes 331, as shown in FIG. 10B, that match corresponding holes formed in the outside surface of the u-shaped channel 323 of the wing 320. The shielding 330 may be positioned on the outside of a u-shaped channel 323, and a clamp plate 332 with matching holes 333 (see FIG. 10C) may be positioned atop of the shielding 330 and aligned with the u-shaped channel 323. The resulting assembly may be held together with screws, bolts, nuts, etc. Grooves 334 formed on the inside of the clamp plate 332 (see inner edge at right in FIG. 10C) may be provided to frictionally grip the shielding 330 to prevent the shielding from sagging between attachment points, for example.

Figure 11:
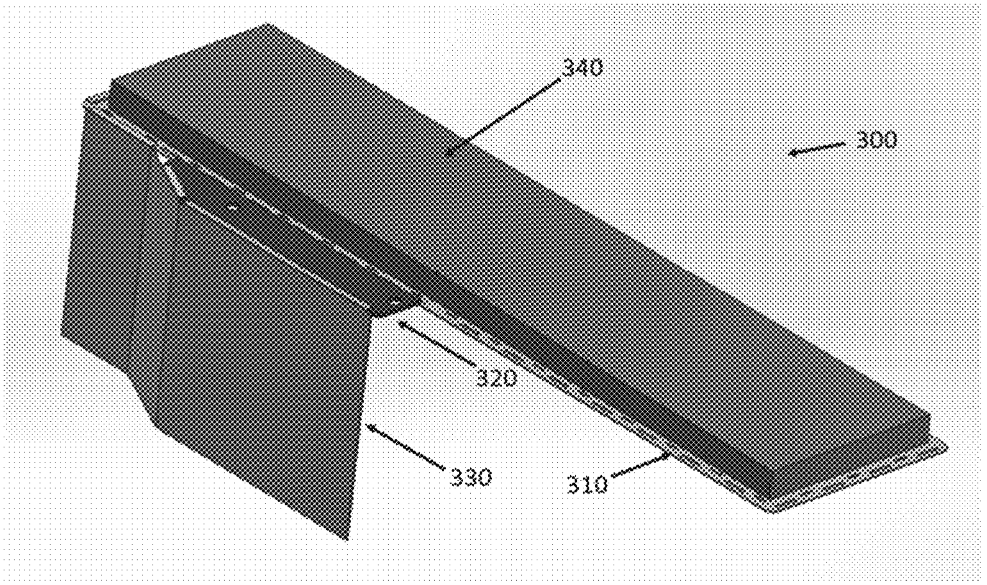
FIG. 11 is a top perspective view of a base unit, shielding, and mattress of a shielding array support system according to some embodiments of this disclosure.

FIG. 11 is a top perspective view of a shielding array support system 300 according to some embodiments of this disclosure. The shielding array support system 300 shown in FIG. 11 comprises a base unit 310, having a wing 320 and shielding 330 removably mounted thereon (e.g., via the use of slots/holes 312 and corresponding tabs 322, 324), and a mattress 340 positioned on an upper surface of base unit 310.

Figure 12:
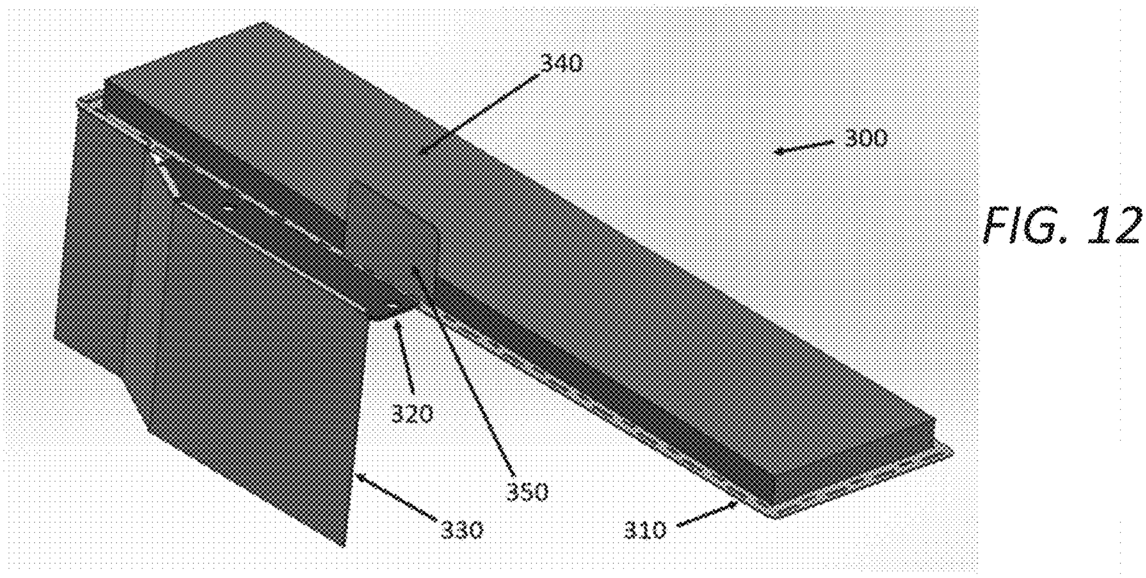
FIG. 12 is a top perspective view of a base unit, shielding, mattress, and an accessory shield of a shielding array support system according to some embodiments of this disclosure.

FIG. 12 is a top perspective view of a shielding array support system 300 according to some embodiments of this disclosure. The shielding array support system 300 shown in FIG. 12 may comprise a base unit 310, one or more wings 320 and or shielding 330 removably and/or repositionably placed about the base unit 310 (e.g., via the use of slots/holes 312 and corresponding tabs 322, 324), a mattress 340, and an accessory shield 350. In the exemplary embodiment depicted in FIG. 12, the accessory shield 350 is removably mounted into an inner row or series of holes/slots 312 formed in a periphery of base unit 310, and is shown in a radiation protection position (e.g., as it might be situated during an x-ray imaging procedure, for example, extending upwardly from base unit 310 in the embodiment depicted in FIG. 12). In the example shown, the placement of mattress 340 on base unit 310 leaves an inner row and an outer row of holes/slots 312 exposed for potential use in removably mounting accessories. For example, the use of an outer row of holes/slots 312 for the removable mounting of wing 320 and shielding 330 leaves an inner row of holes/slots 312 available for the removable mounting of additional components, such as accessory shield 350, as shown in FIG. 12. Thus, shielding array support system 300 may comprise a plurality of shielding elements 330, 350 positioned near the periphery of base unit 310.

Figure 13A:
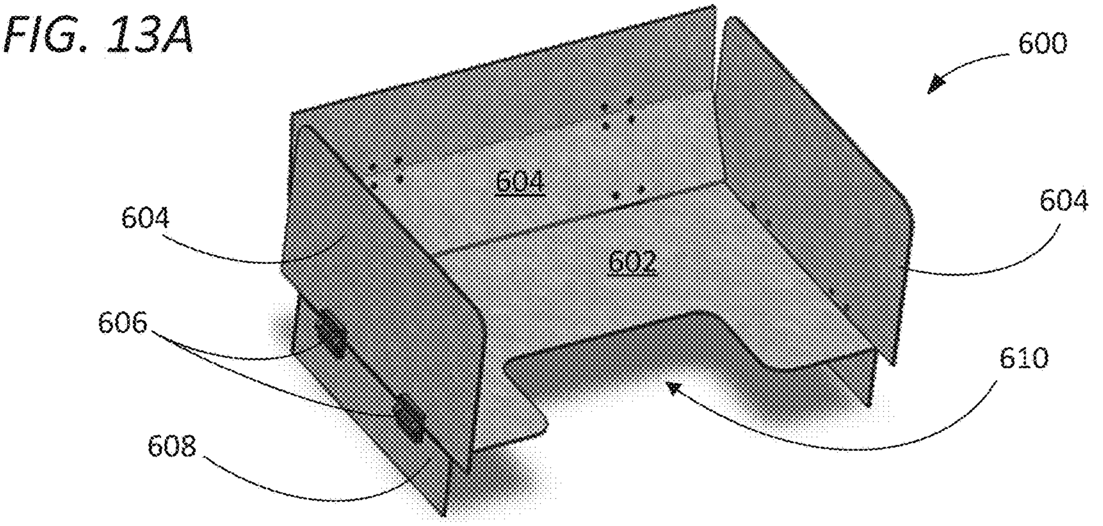
FIGS. 13A-13C are perspective views of an optional patient head shield (unitary configuration) for use with a shielding array support system according to some embodiments of this disclosure.
Figure 13B:
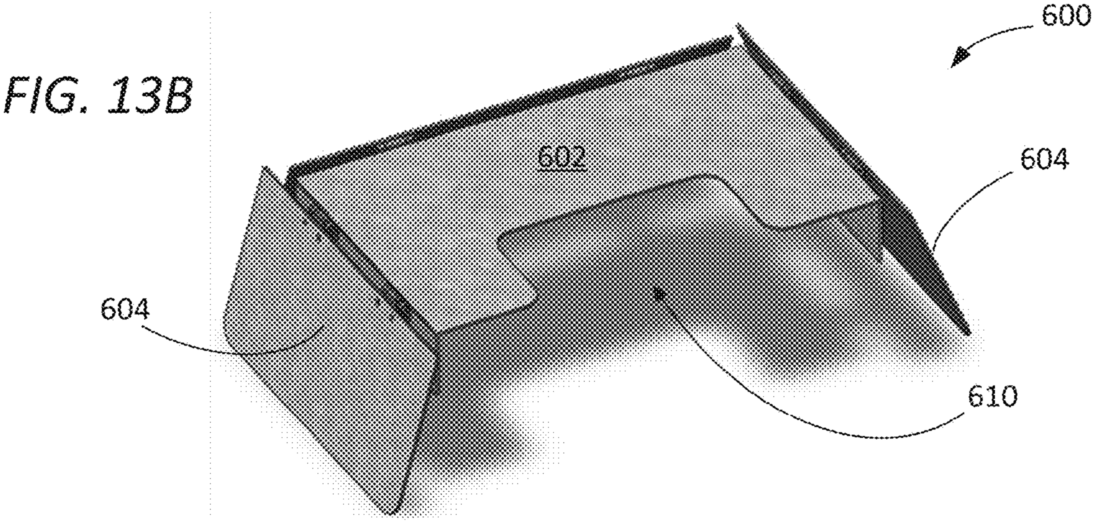
Figure 13C:
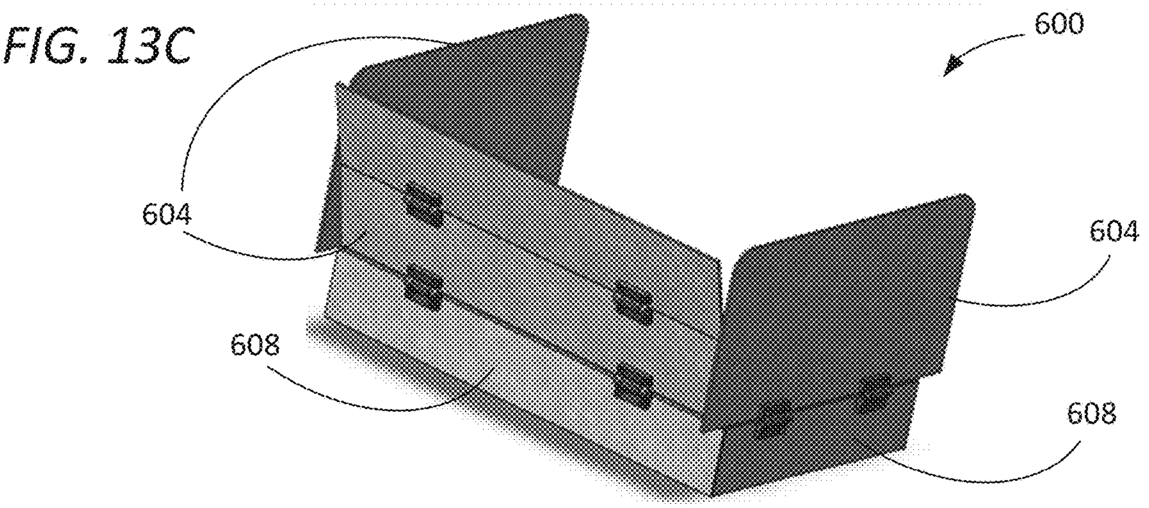

FIGS. 13A-13C are perspective views of an optional patient head shield 600, which may be used in conjunction with the shielding systems 100, 200, 300 described herein. For example, FIG. 13A shows a top perspective view of a patient head shield 600, which may be employed in conjunction with the radiation shielding systems disclosed herein to provide some protection to the head area of a patient from scatter radiation, for example. The particular patient head shield 600 depicted in FIG. 13A is a “unitary” configuration, having a base portion 602, side and/or back panels 604, optional lower panels 608, and an arrangement of hinges 606 to enable pivotable repositioning of the panels 604, 608 as desired. Base portion 602 and panels 604, 608 may be constructed of radiation blocking material. In some embodiments, an optional cutout 610 may be formed in base portion 602 to accommodate positioning of the patient’s head and/or neck relative to the patient head shield 600.

In FIG. 13B, the exemplary unitary patient head shield 600 is shown having one or more of the side and/or back panels 604 adjusted to a downward positioning. This “open” configuration may be employed, for example, during initial positioning of a patient on the patient head shield 600 (e.g., to facilitate ease of movement thereon). The side and/or back panels 604 may then be adjusted to an “upright” position for shielding the patient’s head area (e.g., substantially as shown in FIG. 13A above) just before performing an imaging procedure using x-ray radiation, for example. Patient head shield 600 may be held in place, for example, by the weight of the patient head shield 600 and/or via engagement into holes/slots 312, or via friction fit on a mattress disposed on the procedure table. FIG. 13C is a rear perspective view of the unitary patient head shield 600 of FIGS. 13A and 13B (with panels 604 in an upright or ready position).

Figure 14A:
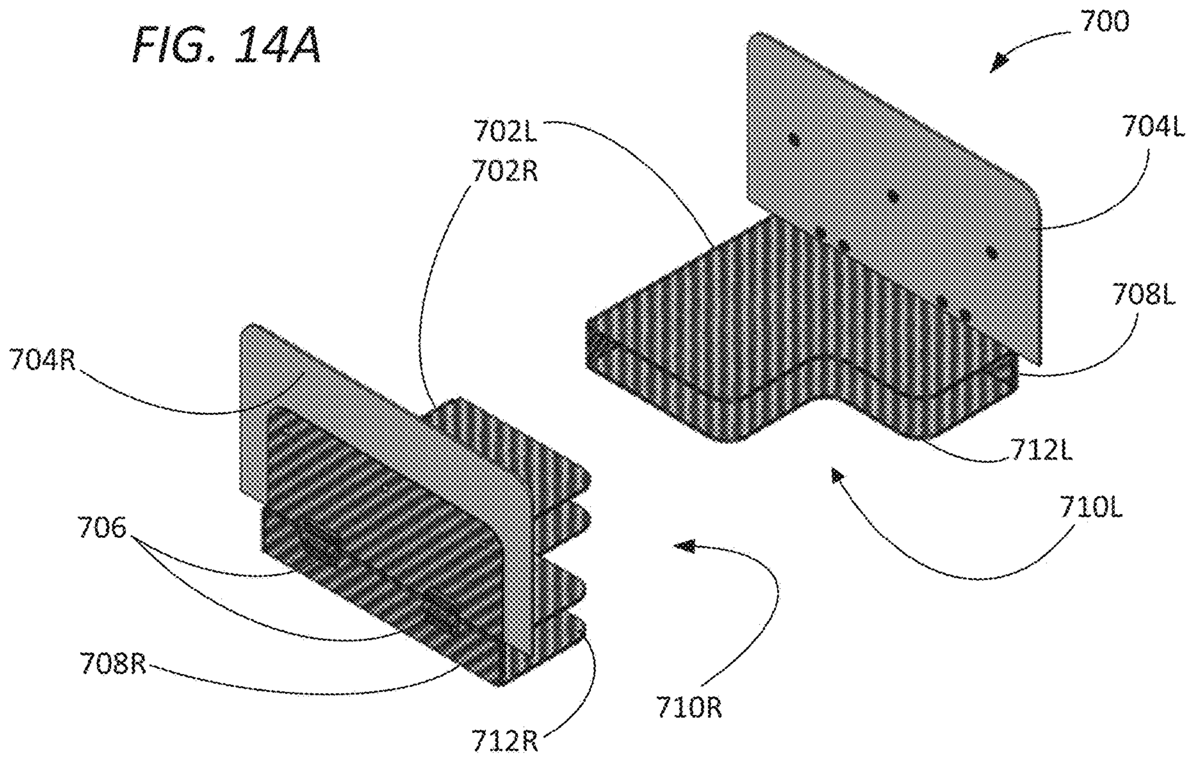
FIGS. 14A-14B are perspective views of an optional patient head shield (two-piece configuration) for use with a shielding array support system according to some embodiments of this disclosure.
Figure 14B:
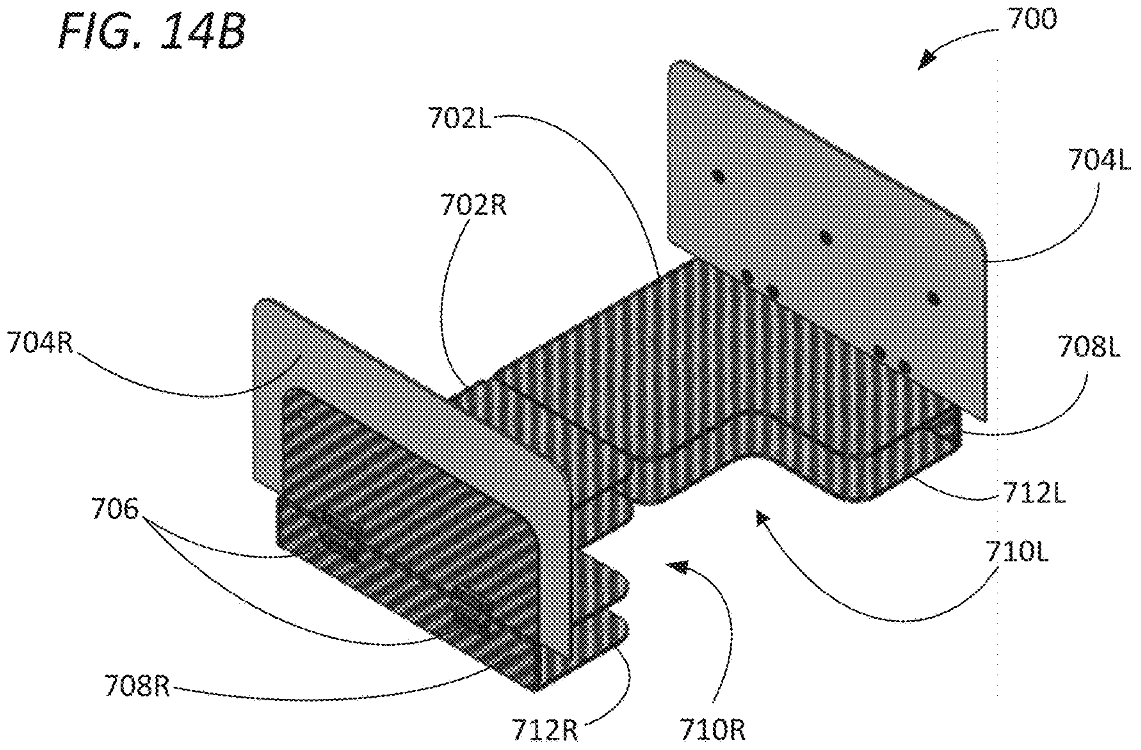

FIGS. 14A-14B are perspective views of an alternative embodiment of an optional patient head shield 700, which may be used in conjunction with the shielding systems 100, 200, 300 described herein. For example, FIG. 14A shows a top perspective view of a patient head shield 700, which may be employed in conjunction with the radiation shielding systems disclosed herein to provide some protection to the head area of a patient from scatter radiation, for example. The particular patient head shield 700 depicted in FIG. 14A is a “two-piece” configuration, having corresponding left and right “halves” as shown: base portions 702L and 702R, left and right side panels 704L and 704R, lower panels 708L and 708R, and an arrangement of hinges 706 to enable pivotable repositioning of the panels 704L/R and 708L/R, as desired. Base portion 702L/R and panels 704L/R may be constructed of radiation blocking material. In some embodiments, optional cutouts 710L/R may be formed in base portions 702L/R to accommodate positioning of the patient’s head and/or neck relative to the patient head shield 700. FIG. 14A also shows an optional feature comprising secondary base portions 712L and 712R, which are similar in shape and arrangement to base portions 702L and 702R, but which are positioned beneath base portions 702L and 702R and connected thereto via lower panels 708L and 708R, for example. Thus, the patient head shield 700 may be held in position in such an embodiment by sandwiching the mattress between the upper base portions 702L, 702R and the lower base portions 712L and 712R. FIG. 14B shows the patient head shield 700 with the left and right “halves” pushed together as it would be arranged during use in conjunction with certain imaging procedures, for example.

Various examples have been described. These and other variations that would be apparent to those of ordinary skill in this field are within the scope of this disclosure.

What is claimed is:

1. A system for reducing scatter radiation during x-ray imaging procedures, the system comprising:

a belt portion having radiation-shielding properties and adapted for placement over and at least partially across an upward-facing surface of a patient positioned on an imaging procedure table, the belt portion having a length configured to extend at least partially across a width of the imaging procedure table, the belt portion having a generally horizontal dimension that is deformable to conform to the upward-facing surface of the patient, the belt portion having a vertical dimension that extends upwardly from the generally horizontal dimension of the belt portion and extends the length of the belt portion along an edge of the belt portion to form a vertically oriented abutting surface adjacent a horizontally oriented surface of the belt portion when the belt portion is placed across the portion of the patient; and a shield portion having radiation-shielding properties and configured to facilitate being selectively moved from a position above the patient into releasable engagement with the abutting surface of the belt portion, a lower portion of the shield portion forming a junction between the belt portion and the shield portion extending at least partially across the width of the imaging procedure table to form a barrier to scatter radiation at the junction, the shield portion comprising one or more panels configured to extend upward generally vertically from the patient when the shield portion is engaged with the belt portion, the shield portion comprising a table attachment extending therefrom, the table attachment configured to mate with a receiver formed in the imaging procedure table for releasably coupling the shield portion to the imaging procedure table.

2. The system for reducing scatter radiation of claim 1 further comprising one or more engagement sensors disposed along the junction, the one or more engagement sensors configured to sense an engagement between the shield portion and the belt portion at the junction.

3. The system for reducing scatter radiation of claim 1 further comprising one or more radiation detection sensors disposed proximate the procedure table and configured to indicate a level of x-ray radiation intensity.

4. The system for reducing scatter radiation of claim 1 wherein the belt portion comprises a plurality of slits to facilitate conforming of the belt portion to an upper surface of the patient.

5. The system for reducing scatter radiation of claim 1 wherein the belt portion comprises a plurality of undulations in a lower portion of the belt portion to facilitate conforming of the belt portion to an upper surface of the patient.

6. The system for reducing scatter radiation of claim 1 wherein the belt portion releasably engages with the shield portion via one or more magnetic elements disposed along the junction between the belt portion and the shield portion.

7. The system for reducing scatter radiation of claim 1 wherein the belt portion releasably engages with the shield portion via one or more hook and loop fasteners disposed along the junction between the belt portion and the shield portion.

8. The system for reducing scatter radiation of claim 2 wherein the one or more engagement sensors disposed along the junction comprises one or more of a pressure sensor, a Hall effect sensor, and a magnetic sensor.

9. The system for reducing scatter radiation of claim 8 wherein the one or more engagement sensors comprises a magnetic sensor configured to sense a degree of engagement between the shield portion and the belt portion at the junction.

10. The system for reducing scatter radiation of claim 8 wherein the one or more engagement sensors comprises a magnetic sensor configured to enhance the engagement between the shield portion and the belt portion at the junction.

11. The system for reducing scatter radiation of claim 1 wherein the belt portion and the shield portion do not restrict access to the patient when the shield portion is in releasable engagement with the belt portion.

12. The system for reducing scatter radiation of claim 1 wherein the belt portion and the shield portion do not form an enclosed volume around a portion of the patient when the shield portion is in releasable engagement with the belt portion.

13. The system for reducing scatter radiation of claim 1 wherein the belt portion has an elongate shape.

14. The system for reducing scatter radiation of claim 13 wherein the elongate shape comprises a tubular shape.

15. The system for reducing scatter radiation of claim 13 wherein the elongate shape comprises a generally rectangular cross-section.

* * * * *